US009273091B2

(12) United States Patent
Vlahov et al.

(10) Patent No.: US 9,273,091 B2
(45) Date of Patent: *Mar. 1, 2016

(54) PROCESSES FOR PREPARING TUBULYSINS

(71) Applicant: ENDOCYTE, INC., West Lafayette, IN (US)

(72) Inventors: Iontcho Radoslavov Vlahov, West Lafayette, IN (US); Michael Groaning, West Lafayette, IN (US); Paul Joseph Kleindl, Lebanon, IN (US); Hari Krishna R. Santhapuram, West Lafayette, IN (US); Fei You, West Lafayette, IN (US); Kevin Yu Wang, Zionsville, IN (US); Le-Cun Xu, West Lafayette, IN (US); Katheryn Marie Stanford, Lafayette, IN (US); Allen Ritter, Lafayette, IN (US); Christopher Paul Leamon, West Lafayette, IN (US)

(73) Assignee: Endocyte, Inc., West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/518,568

(22) Filed: Oct. 20, 2014

(65) Prior Publication Data

US 2015/0225447 A1 Aug. 13, 2015

Related U.S. Application Data

(63) Continuation of application No. 13/814,336, filed as application No. PCT/US2011/046797 on Aug. 5, 2011, now Pat. No. 8,889,880.

(60) Provisional application No. 61/371,433, filed on Aug. 6, 2010.

(51) Int. Cl.
*C07D 227/04* (2006.01)
*C07K 5/02* (2006.01)
*A61K 31/445* (2006.01)
*C07D 417/12* (2006.01)

(52) U.S. Cl.
CPC ............... *C07K 5/02* (2013.01); *A61K 31/445* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 5,627,165 A | 5/1997 | Glazier | |
| 7,601,332 B2 | 10/2009 | Vlahov et al. | |
| 7,754,885 B2 | 7/2010 | Hoefle et al. | |
| 7,776,814 B2 | 8/2010 | Dömling et al. | |
| 7,816,377 B2 | 10/2010 | Domling et al. | |
| 8,889,880 B2 * | 11/2014 | Vlahov et al. | 548/146 |
| 2006/0128754 A1 | 6/2006 | Hoefle et al. | |

FOREIGN PATENT DOCUMENTS

| | | |
|---|---|---|
| WO | 2004/005326 | 1/2004 |
| WO | 2004/046170 | 6/2004 |
| WO | 2008/112873 | 11/2008 |
| WO | 2011/069116 | 6/2011 |
| WO | 2011/006639 | 11/2011 |
| WO | 2012/019123 | 2/2012 |

OTHER PUBLICATIONS

Wang, Zhiyong, et al. "Structure-activity and High-content Imaging Analyses of Novel Tubulysins," Chemical Biology & Drug Design 70(2): 75-86, (2007).
Patterson, Andrew W., et al. "Design, synthesis, and biological properties of highly potent tubulysin D analogues," Chemistry—A European Journal 13(34): 9534-9541, (2007).
Steinmetz, Heinrich, et al. "Isolation, crystal and solution structure determination, and biosynthesis of tubulysins—powerful inhibitors of tubulin polymerization from myxobacteria," Angewandte Chemie International Edition 43(37): 4888-4892, (2004).
March, Jerry. Advanced organic chemistry: reactions, mechanisms, and structure. vol. 4. New York: McGraw-Hill, 1968, p. 362-363, 816, 885, 896.
Lopes, Francisca, Rui Moreira, and Jim Iley. "Acyloxymethyl as a drug protecting group. Part 5.1 Kinetics and mechanism of the hydrolysis of tertiary N-acyloxymethylsulfonamides," J. Chem. Soc., Perkin Trans. 2, vol. 3: 431-440, (1999).
Churlaud, Carine, et al., "Novel 4-(Trimethylsilyl)aminoalkanes and 4-(Trimethylsilyl)aminoalk-2-enes, via a 1.5-Hydride Shift, in the Reaction of r-Unsaturated Silanes with Aminomethylbenzotriazoles," Organometallics, 18(21): 4270-4274.
Peltier, Hillary M., et al. "The total synthesis of tubulysin D," Journal of the American Chemical Society 128(50): 16018-16019 (2006).
Wu, Shih Hsiung, Zhi Wei Guo, and Charles J. Sih. "Enhancing the enantioselectivity of Candida lipase-catalyzed ester hydrolysis via noncovalent enzyme modification," Journal of the American Chemical Society 112(5) (1990).
Sasse, F., et al. "Tubulysins, new cytostatic peptides from myxobacteria acting on microtubuli. Production, isolation, physicochemical and biological properties," J Antibiot 53:879-885 (2000).
Kaur, G., et al., "Biological evaluation of tubulysin A: a potential anticancer and antiangiogenic natural product," Biochem. J. 396, 235-242, (2006).
Domling, A., et al., "Myxobacterial epothilones and tubulysins as promising anticancer agents," Mol. Diversity, 9:141-147, (2005).
Pando, O., et al, "First Total Synthesis of Tubulysin B." Org. Lett., 11(24): 5567-5569, (2009).
G. Hofle, G., et al., "Semisynthesis and degradation of the tubulin inhibitors epothilone and tubulysin," Pure Appi. Chem. 75:167-178, (2003).

(Continued)

*Primary Examiner* — Heidi Reese
(74) *Attorney, Agent, or Firm* — Barnes & Thornburg LLP

(57) ABSTRACT

Tubulysins are a series of naturally occurring cytotoxic agents that are of interest as anticancer therapeutic agents. Processes and intermediates useful for preparing naturally occurring and non-naturally occurring tubulysins and analogs and derivatives thereof are described.

20 Claims, No Drawings

(56) References Cited

OTHER PUBLICATIONS

Rose, "Taxol-based combination chemotherapy and other in vivo preclinical antitumor studies," J Natl Cancer Inst Monogr, 15:47-53 (1993).

Lee et al., "BMS-247550: a novel epothilone analog with a mode of action similar to paclitaxel but possessing superior antitumor efficacy," Clin Cancer Res 7:1429-1437 (2001).

PCT Search Report and Written Opinion for PCT/US2011/046797, completed Dec. 23, 2011.

Speckamp, et al., "New Developments in the Chemistry of N-Acyliminium Ions and Related Intermediates," Tetrahedron 56(24):3817-3856 (2000).

European Search Report prepared for corresponding European Application Serial No. 08841521.1, mailed Jul. 18, 2011.

Raghavan, Bhooma, et al. "Cytotoxic Simplified Tubulysin Analogues," J. Med. Chem. 51:1530-1533 (2008).

PCT Search Report and Written Opinion for PCT/EP2003/011603, completed Feb. 11, 2011.

Patterson, Andrew W., IIillary M. Peltier, and Jonathan A. Ellman. "Expedient synthesis of N-methyl tubulysin analogues with high cytotoxicity," The Journal of Organic Chemistry, 73(12): 4362-4369 (2008).

* cited by examiner

PROCESSES FOR PREPARING TUBULYSINS

CROSS-REFERENCE TO RELATED APPLICATIONS

This application is a continuation of U.S. application Ser. No. 13/814,336 filed on Feb. 5, 2013, which is a national stage entry under 35 USC §371(b) of International Application No. PCT/US2011/046797, filed Aug. 5, 2011, which claims priority under 35 U.S.C. §119(e) to U.S. Provisional Application Serial No. 61/371,433 filed on Aug. 6, 2010, the entire disclosures of which are incorporated herein by reference.

TECHNICAL FIELD

The invention described herein pertains to processes for preparing tubulysins.

BACKGROUND AND SUMMARY OF THE INVENTION

The tubulysins are members of a new class of natural products isolated from myxobacterial species (F. Sasse, et al., *J. Antibiot.* 2000, 53, 879-885). As cytoskeleton interacting agents, the tubulysins are mitotic poisons that inhibit tubulin polymerization and lead to cell cycle arrest and apoptosis (H. Steinmetz, et al., *Chem. Int. Ed.* 2004, 43, 4888-4892; M. Khalil, et al., *ChemBioChem.* 2006, 7, 678-683; G. Kaur, et al., *Biochem. J.* 2006, 396, 235-242). Tubulysins are extremely potent cytotoxic molecules, exceeding the cell growth inhibition of any clinically relevant traditional chemotherapeutic e.g. epothilones, paclitaxel, and vinblastine. Furthermore, they are potent against multidrug resistant cell lines (A. Dömling, et al., *Mol. Diversity* 2005, 9, 141-147). These compounds show high cytotoxicity tested against a panel of cancer cell lines with $IC_{50}$ values in the low picomolar range; thus, they are of interest as potential anticancer therapeutics.

Tubulysins are described herein. Structurally, tubulysins often include linear tetrapeptoid backbones, including illustrative compounds having formula T

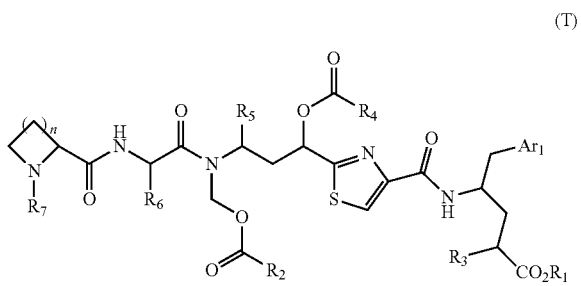

(T)

and pharmaceutically acceptable salts thereof;
wherein
$Ar_1$ is optionally substituted aryl;
$R_1$ is hydrogen, alkyl, arylalkyl or a pro-drug forming group;
$R_2$ is selected from the group consisting of optionally substituted alkyl and optionally substituted cycloalkyl;
$R_4$ is optionally substituted alkyl or optionally substituted cycloalkyl;
$R_3$ is optionally substituted alkyl;
$R_5$ and $R_6$ are each independently selected from the group consisting of optionally substituted alkyl and optionally substituted cycloalkyl;
$R_7$ is optionally substituted alkyl; and
n is 1, 2, 3, or 4.

Another illustrative group of tubulysins described herein are more particularly comprised of one or more non-naturally occurring or hydrophobic amino acid segments, such as N-methyl pipecolic acid (Mep), isoleucine (Ile),

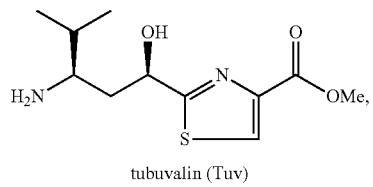

tubuvalin (Tuv)

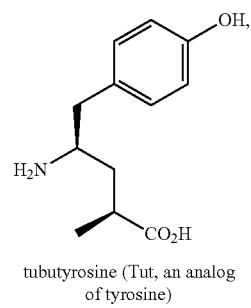

tubutyrosine (Tut, an analog of tyrosine)

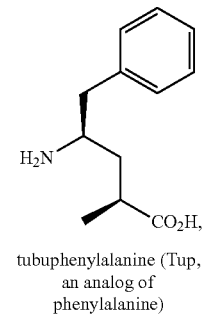

tubuphenylalanine (Tup, an analog of phenylalanine)

and analogs and derivative of each of the foregoing. A common feature in the molecular architecture of the more potent natural occurring tubulysins is the acid and/or base sensitive N-acyloxymethyl substituent (or a N,O-acetal of formaldehyde) represented by R2-C(O) in the formula (T).

Another illustrative group of tubulysins described herein are those having formula 1.

Formula 1

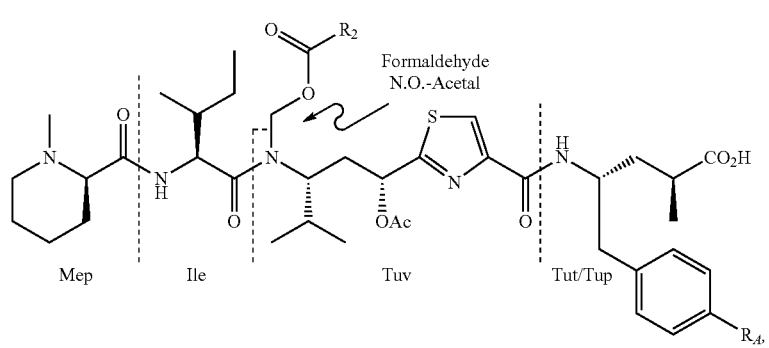

Structures of several natural tubulysins

| Tubulysin | $R_A$ | $R_2$ |
|---|---|---|
| A | OH | $CH_2CH(CH_3)_2$ |
| B | OH | $CH_2CH_2CH_3$ |
| C | OH | $CH_2CH_3$ |
| D | H | $CH_2CH(CH_3)_2$ |
| E | H | $CH_2CH_2CH_3$ |
| F | H | $CH_2CH_3$ |
| G | OH | $CH=C(CH_3)_2$ |
| H | H | $CH_3$ |
| I | OH | $CH_3$ |

A total synthesis of tubulysin D possessing C-terminal tubuphenylalanine ($R_A$=H) (H. Peltier, et al., J. Am. Chem. Soc. 2006, 128, 16018-16019) has been reported. Recently, a modified synthetic protocol toward the synthesis of tubulysin B ($R_A$=OH) (O. Pando, et at., Org. Lett. 2009, 11, 5567-5569) has been reported. However, attempts to follow the published procedures to provide larger quantities of tubulysins were unsuccessful, being hampered in part by low yields, difficult to remove impurities, the need for expensive chromatographic steps, and/or the lack of reproducibility of several steps. The interest in using tubulysins for anticancer therapeutics accents the need for reliable and efficient processes for preparing tubulysins, and analogs and derivatives thereof. Described herein are improved processes for making natural tubulysins, or analogs or derivatives thereof, including compounds of formula (T) and formula (1).

In one illustrative embodiment of the invention, processes for preparing natural tubulysins, or analogs or derivatives thereof, including compounds of formula (T) and formula (1) are described herein. The processes include one or more steps described herein. In another embodiment, a process is described for preparing a compound of formula B, wherein $R_5$ and $R_6$ are as described in the various embodiments herein, such as each being independently selected from optionally substituted alkyl or optionally substituted cycloalkyl; and $R_8$ is C1-C6 n-alkyl; wherein the process comprises the step of treating a compound of formula A with a silylating agent, such as triethylsilyl chloride, and a base, such as imidazole in an aprotic solvent.

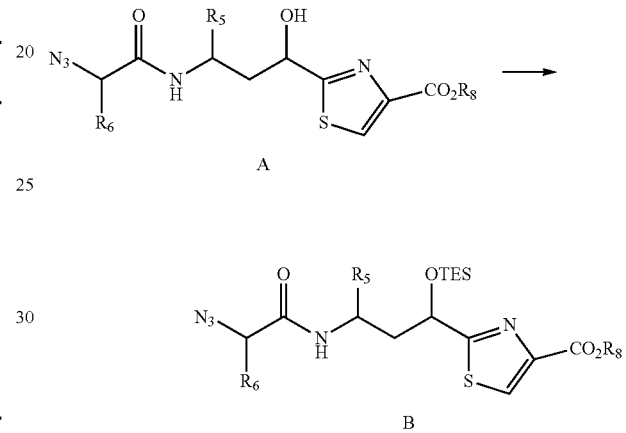

It is to be understood that $R_5$ and $R_6$ may each include conventional protection groups on the optional substituents.

In another embodiment, a process is described for preparing a compound of formula C, wherein $R_5$ and $R_6$ are as described in the various embodiments herein, such as each being independently selected from optionally substituted alkyl or optionally substituted cycloalkyl; $R_8$ is C1-C6 n-alkyl; and $R_2$ is as described in the various embodiments herein, such as being selected from optionally substituted alkyl or optionally substituted cycloalkyl; wherein the process comprises the step of treating a compound of formula B with a base and a compound of the formula $ClCH_2OC(O)R_2$ in an aprotic solvent at a temperature below ambient temperature, such as in the range from about −78° C. to about 0° C.; wherein the molar ratio of the compound of the formula $ClCH_2OC(O)R_2$ to the compound of formula B from about 1 to about 1.5.

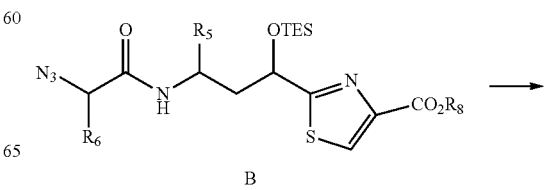

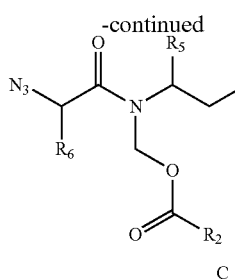

It is to be understood that $R_2$, $R_5$ and $R_6$ may each include conventional protection groups on the optional substituents.

In another embodiment, a process is described for preparing a compound of formula D, wherein $R_5$ and $R_6$ are as described in the various embodiments herein, such as being selected from optionally substituted alkyl or optionally substituted cycloalkyl; $R_8$ is C1-C6 n-alkyl; $R_2$ is as described in the various embodiments herein, such as being selected from optionally substituted alkyl or optionally substituted cycloalkyl; and $R_7$ is optionally substituted alkyl; wherein the process comprises the steps of a) preparing a compound of formula (E1) where $X_1$ is a leaving group from a compound of formula E; and b) treating a compound of formula C under reducing conditions in the presence of the compound of formula E1.

optionally substituted alkyl; wherein the process comprises the step of treating compound D with a hydrolase enzyme.

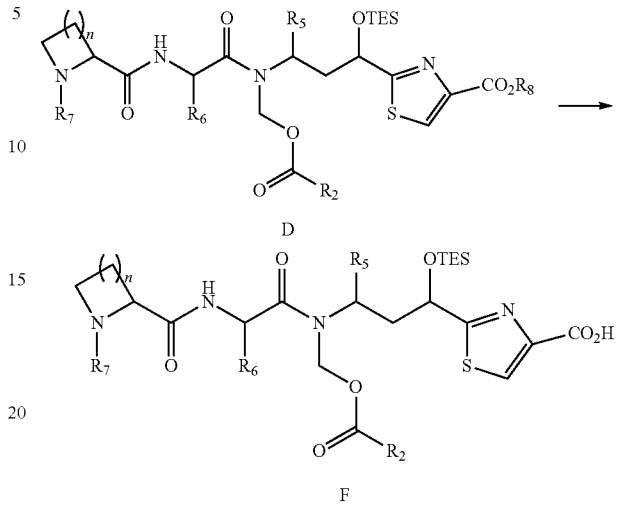

It is to be understood that $R_2$, $R_5$, $R_6$, and $R_7$ may each include conventional protection groups on the optional substituents.

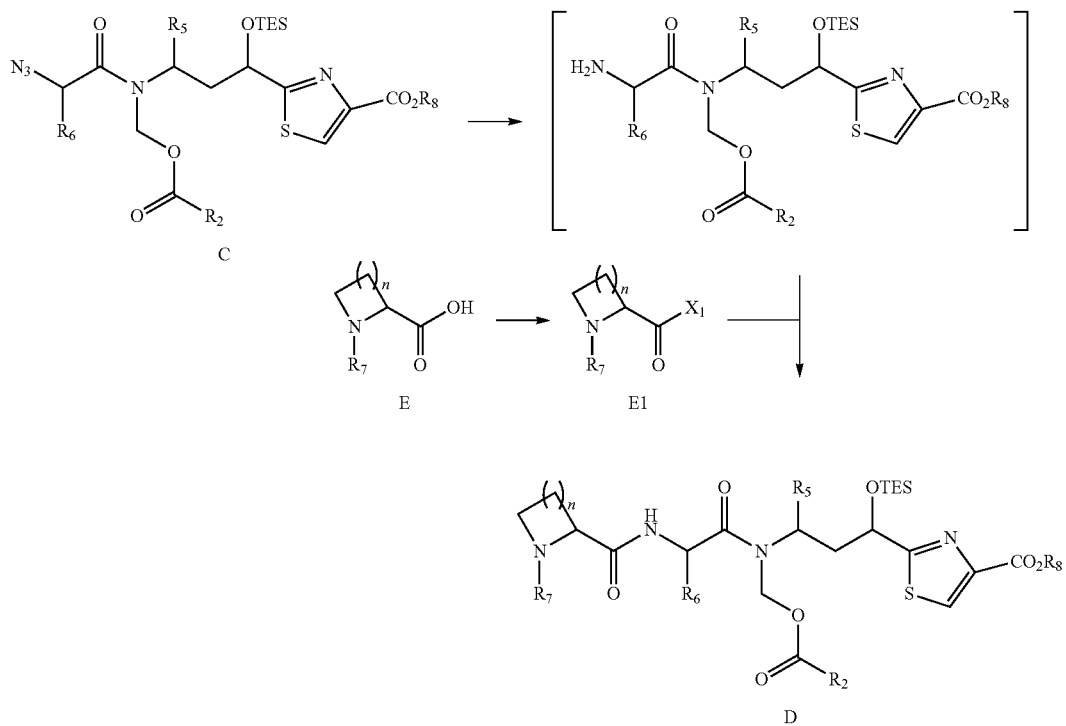

It is to be understood that $R_2$, $R_5$, $R_6$, and $R_7$ may each include conventional protection groups on the optional substituents.

In another embodiment, a process is described for preparing a compound of formula F, wherein $R_5$ and $R_6$ are as described in the various embodiments herein, such as being selected from optionally substituted alkyl or optionally substituted cycloalkyl; $R_2$ is as described in the various embodiments herein, such as being selected from optionally substituted alkyl or optionally substituted cycloalkyl; and $R_7$ is In another embodiment, a process is described for preparing a compound of formula G, wherein $R_5$ and $R_6$ are as described in the various embodiments herein, such as being selected from optionally substituted alkyl or optionally substituted cycloalkyl; $R_2$ is as described in the various embodiments herein, such as being selected from optionally substituted alkyl or optionally substituted cycloalkyl; and $R_7$ is optionally substituted alkyl; wherein the process comprises the step of treating the silyl ether of compound F with a non-basic fluoride containing reagent.

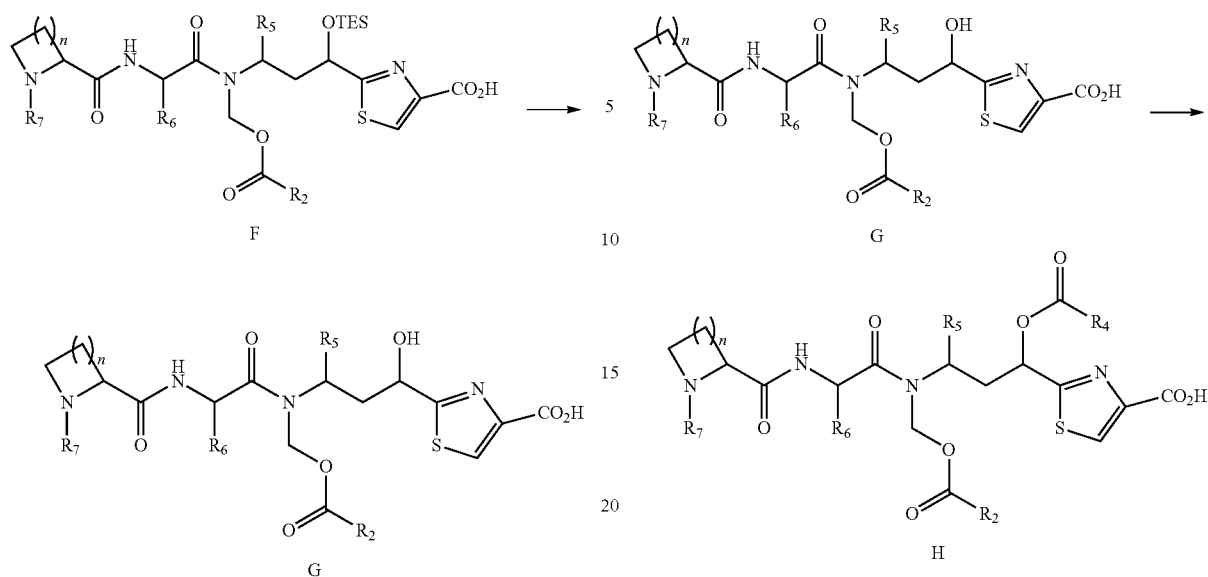

It is to be understood that $R_2$, $R_5$, $R_6$, and $R_7$ may each include conventional protection groups on the optional substituents.

In another process is described for preparing a compound of formula H, wherein $R_5$ and $R_6$ are as described in the various embodiments herein, such as being selected from optionally substituted alkyl or optionally substituted cycloalkyl; $R_2$ and $R_4$ are as described in the various embodiments herein, such as being selected from optionally substituted alkyl or optionally substituted cycloalkyl; and $R_7$ is optionally substituted alkyl; wherein the process comprises the step of treating a compound of formula G with an acylating agent of formula $R_4C(O)X_2$, where $X_2$ is a leaving group.

It is to be understood that $R_2$, $R_4$, $R_5$, $R_6$, and $R_7$ may each include conventional protection groups on the optional substituents.

In another embodiment, a process is described for preparing a tubulysin of formula (T), wherein $Ar_1$ is optionally substituted aryl; $R_1$ is hydrogen, optionally substituted alkyl, optionally substituted arylalkyl or a pro-drug forming group; $R_5$ and $R_6$ are as described in the various embodiments herein, such as being selected from optionally substituted alkyl or optionally substituted cycloalkyl; $R_3$ is optionally substituted alkyl; $R_2$ and $R_4$ are as described in the various embodiments herein, such as being selected from optionally substituted alkyl or optionally substituted cycloalkyl; and $R_7$ is optionally substituted alkyl; wherein the process comprises the step of forming an active ester intermediate from a compound of formula H; and reacting the active ester intermediate with a compound of the formula I to give a compound of the formula T.

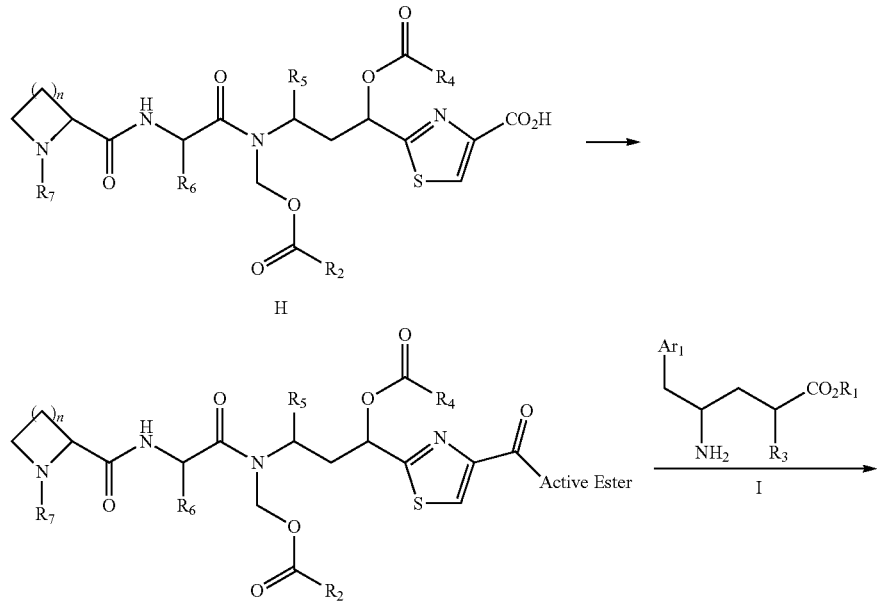

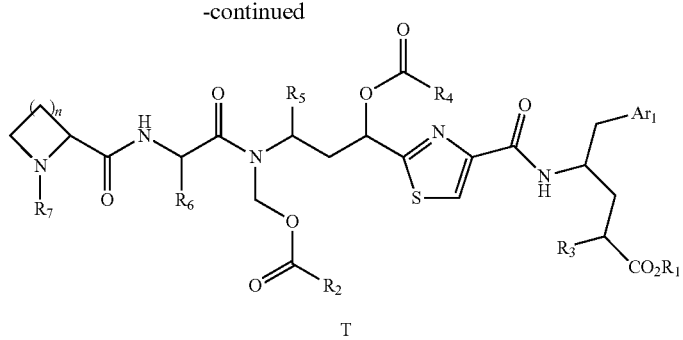

T

It is to be understood that $Ar_1$, $R_1$, $R_2$, $R_4$, $R_5$, $R_6$, and $R_7$ may each include conventional protection groups on the optional substituents.

DETAILED DESCRIPTION

In one embodiment, a process is described for preparing a compound of formula B, wherein $R_5$ and $R_6$ are as described in the various embodiments herein, such as being selected from optionally substituted alkyl or optionally substituted cycloalkyl; and $R_8$ is C1-C6 n-alkyl; wherein the process comprises the step of treating a compound of formula A with triethylsilyl chloride and imidazole in an aprotic solvent.

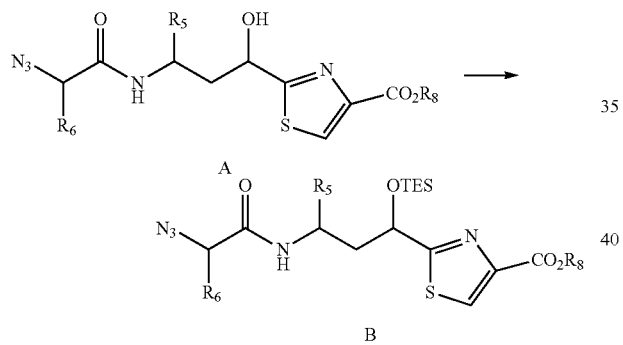

In the previously reported preparations of the intermediate silyl ether of formula 2, use of a large excess of triethylsilyl trifluoromethylsulfonate (TESOTf) and lutidine is described (see, for example, Peltier, et al., 2006). It was found that the reported process makes it necessary to submit the product of the reaction to a chromatographic purification step. Contrary to that reported, it has been surprisingly discovered herein that the less reactive reagent TESCl may be used. It has also been surprisingly discovered herein that although TESCl is a less reactive reagent, it may nonetheless be used in nearly stoichiometric amounts in the processes described herein. It is appreciated herein that the use of the less reactive TESCl may also be advantageous when the process is performed on larger scales, where higher reactivity reagents may represent a safety issue. It has also been discovered that the use of TESCl in nearly stoichiometric amounts renders the chromatographic purification step unnecessary. In an alternative of the embodiment, the process is performed without subsequent purification. In another alternative of the foregoing embodiments, and each additional embodiment described herein, $R_5$ is isopropyl. In another alternative of the foregoing embodiments, and each additional embodiment described herein, $R_6$ is sec-butyl. In another alternative of the foregoing embodiments, and each additional embodiment described herein, $R_8$ is methyl. In another alternative of the foregoing embodiments, and each additional embodiment described herein, the silyl ether is TES.

In an illustrative example of the processes described herein, a process for preparing the silyl ether 2 in high yield is described wherein compound 1 is treated with 1.05 equivalent of TESCl and 1.1 equivalent of imidazole.

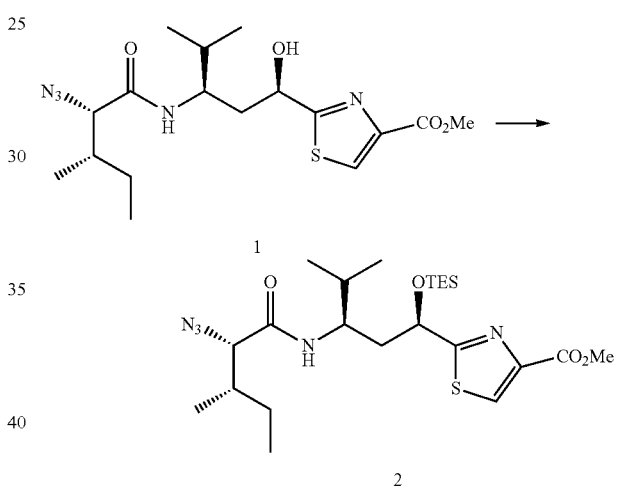

In one alternative of the foregoing example, the compound 2 is nor purified y chromatography.

In another embodiment, a process is described for preparing a compound of formula C, wherein $R_5$ and $R_6$ are each independently selected from the group consisting of optionally substituted alkyl and optionally substituted cycloalkyl; $R_8$ is C1-C6 n-alkyl; and $R_2$ is selected from the group consisting of optionally substituted alkyl and optionally substituted cycloalkyl; wherein the process comprises the step of treating a compound of formula B with from about 1 equivalent to about 1.5 equivalent of base and from about 1 equivalent to about 1.5 equivalent of a compound of the formula $ClCH_2OC(O)R_2$ in an aprotic solvent at a temperature from about −78° C. to about 0° C.

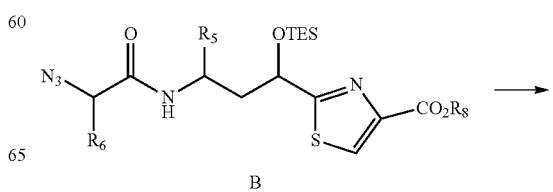

-continued

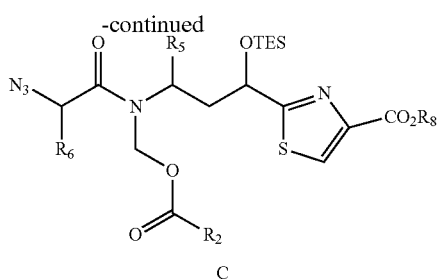

C

In another embodiment, the process of the preceding embodiment is described wherein the compounds of formulae B and C have the stereochemistry shown in the following scheme for B' and C'.

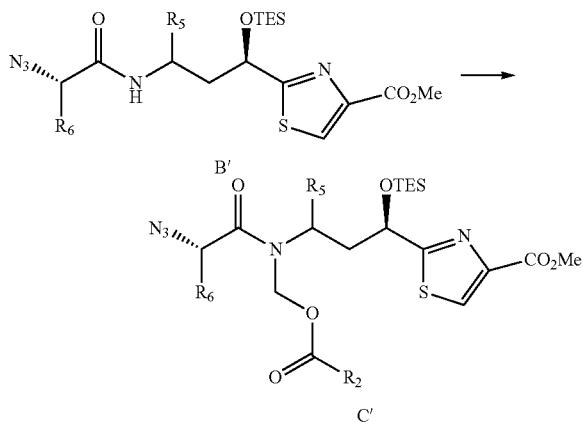

In another illustrative embodiment, the process of any one of the preceding embodiments is described wherein about 1 equivalent to about 1.3 equivalent of a compound of the formula $ClCH_2OC(O)R_2$ is used. In another illustrative example, the process of any one of the preceding embodiments is described, wherein about 1.2 equivalent of a compound of the formula $ClCH_2OC(O)R_2$ is used. In another illustrative example, the process of any one of the preceding embodiments is described wherein $R_2$ is n-propyl. In another alternative of the foregoing embodiments, and each additional embodiment described herein, $R_2$ is $CH_2CH(CH_3)_2$, $CH_2CH_2CH_3$, $CH_2CH_3$, $CH=C(CH_3)_2$, or $CH_3$.

In an illustrative example of the processes described herein, a process for preparing the N,O-acetal 3 is described. In another illustrative example, compound 2 is treated with 1.1 equivalent of potassium hexamethyldisilazane (KHMDS) and 1.2 equivalent of chloromethyl butanoate in a nonprotic solvent at about −45° C. In another illustrative example, the product formed by any of the preceding examples may be used without chromatographic purification.

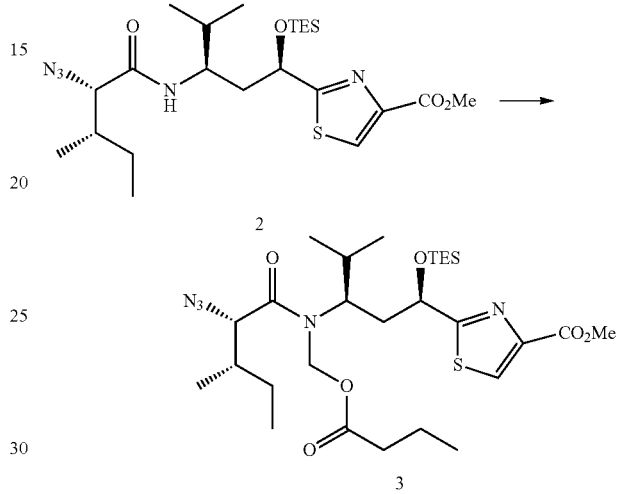

In another embodiment, a process is described for preparing a compound of formula D, wherein $R_5$ and $R_6$ are each independently selected from the group consisting of optionally substituted alkyl and cycloalkyl; $R_8$ is C1-C6 n-alkyl; $R_2$ is selected from the group consisting of optionally substituted alkyl and cycloalkyl; and $R_7$ is optionally substituted alkyl; wherein the process comprises the steps of a) preparing a compound of formula (E1) where $X_1$ is a leaving group from a compound of formula E; and b) treating a compound of formula C under reducing conditions with the compound of formula E1.

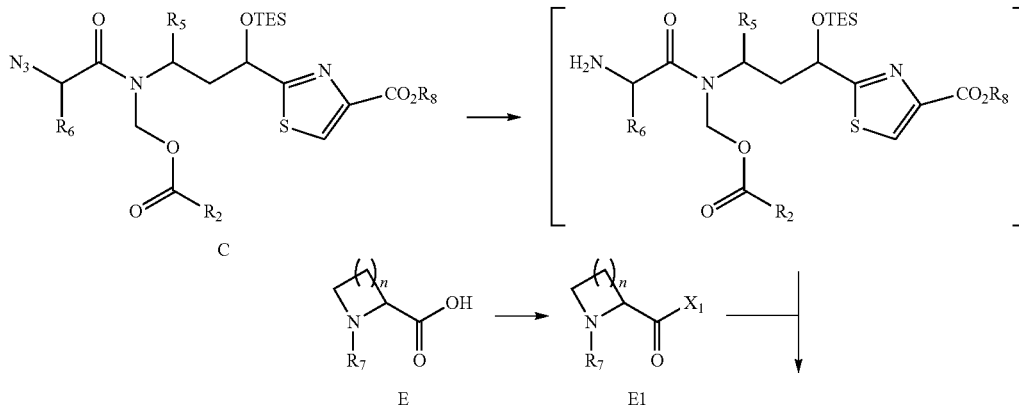

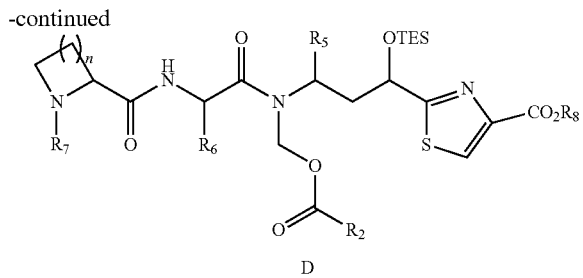

In one illustrative example, a mixture of compound 3 and the pentafluorophenyl ester of D-N-methyl-pipecolic acid is reduced using $H_2$ and a palladium-on-charcoal catalyst (Pd/C) to yield compound 4. It has been discovered herein that epimerization of the active ester of pipecolic acid can occur during reaction or during its preparation or during the reduction under the previously reported reaction conditions. For example, contrary to prior reports indicating that epimerization does not occur (see, for example, Peltier, 2006), upon repeating those reported processes on a larger scale it was found here that substantial amounts of epimerized compounds were formed. In addition, it was discovered herein that substantial amounts of rearrangement products formed by the rearrangement of the butyryl group to compound 8 were formed using the reported processes. Finally, it was discovered herein that the typical yields of the desired products using the previously reported processes were only about half of that reported. It has been discovered herein that using diisopropylcarbodiimide (DIC) and short reaction times lessens that amount of both the unwanted by-product resulting from the epimerization reaction and the by-product resulting from the rearrangement reaction. In another alternative of the foregoing embodiments, and each additional embodiment described herein, n is 3. In another alternative of the foregoing embodiments, and each additional embodiment described herein, $R_7$ is methyl.

In one illustrative example, it was found that limiting the reaction time for the preparation of pentafluorophenyl D-N-methyl-pipecolate to about 1 hour lessened the formation of the diastereomeric tripeptide 9. It has also been discovered that using dry 10% Pd/C as catalyst, rather than a more typically used wet or moist catalyst, lessens the amount of epimer 9 formed during the reduction. It has also been discovered that using dry 10% P/C and/or shorter reaction times also lessens the formation of rearranged amide 8.

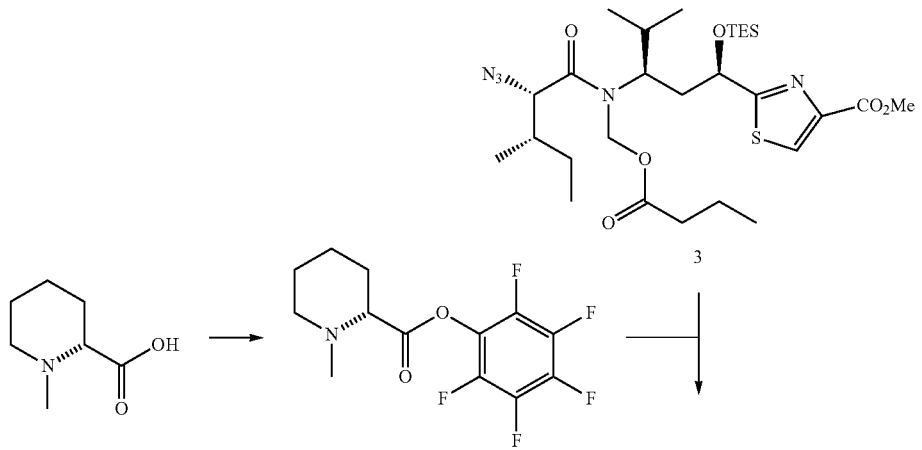

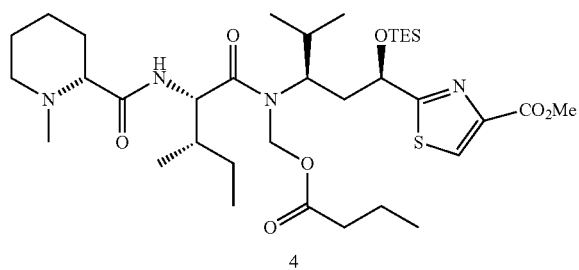

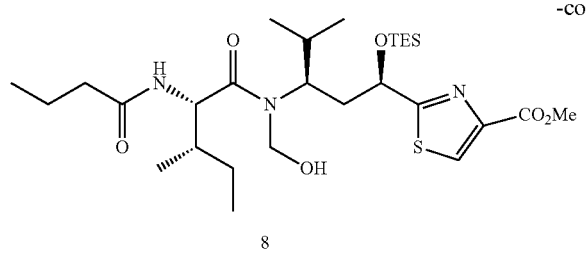

8

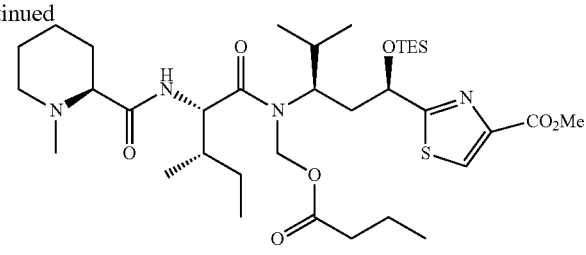

9

It has been previously reported that removal of the protecting group from the secondary hydroxyl group leads to an inseparable mixture of the desired product 5 and a cyclic O,N-acetal side-product as shown in the following scheme.

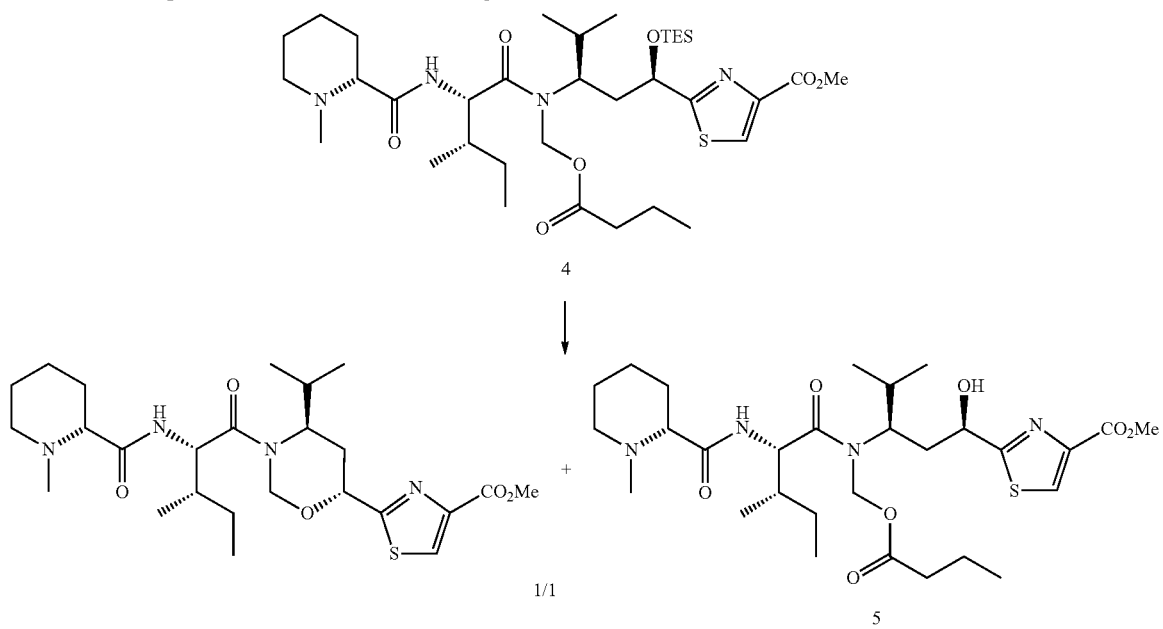

Further, upon repeating the reported process, it has been discovered herein that removal of the methyl ester using basic conditions, followed by acetylation of the hydroxyl group leads to an additional previously unreported side-product, iso-7. That additional side-product is difficult to detect and difficult to separate from the desired compound 7. Without being bound by theory, it is believed herein that iso-7 results from rearrangement of the butyrate group from the N-hydroxymethyl group to the secondary hydroxyl group, as shown below.

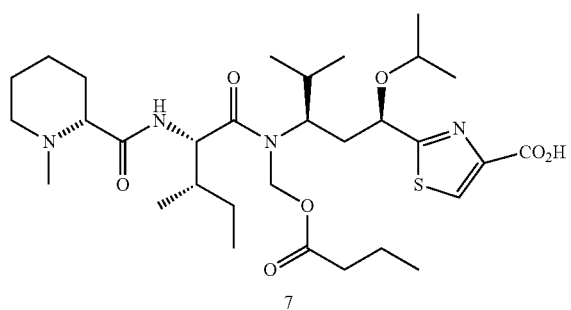

7

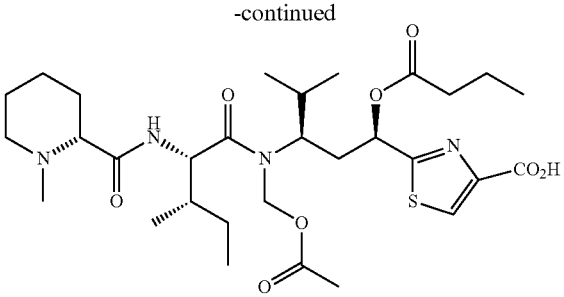

iso-7

It has been discovered that reordering the two deprotection steps and using different conditions for each deprotection reaction results in improved yields of compounds of formula H, such as compound 7, after introduction of the $R_4CO$ group on the secondary hydroxyl group, as further described below.

In another embodiment, a process is described for preparing a compound of formula F, wherein $R_5$ and $R_6$ are each independently selected from the group consisting of optionally substituted alkyl and optionally substituted cycloalkyl; $R_2$ is selected from the group consisting of optionally substituted alkyl and optionally substituted cycloalkyl; and $R_7$ is optionally substituted alkyl; wherein the process comprises the step of treating compound D with a hydrolase enzyme.

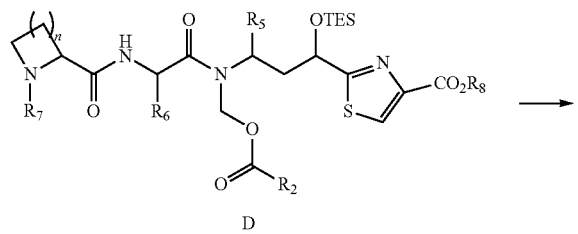

D

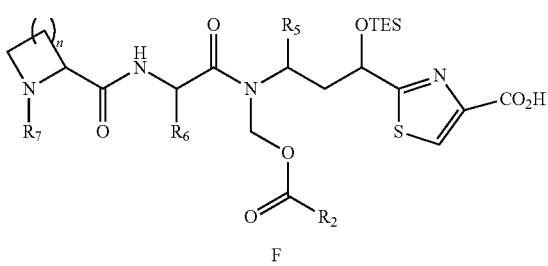

F

In another embodiment, the preceding process wherein the treating step comprises adding a solution of compound D in a water miscible solvent to a buffered solution containing the hydrolase enzyme at a rate which minimizes precipitation of the ester. In another embodiment the ester is added over a period of from about 24 hours to about 100 hours. In another embodiment the ester is added over a period of from about 48 hours to about 100 hours. In another alternative of the foregoing embodiments, and each additional embodiment described herein, $R_8$ is methyl. In another embodiment, the embodiment of any one of the preceding embodiments wherein the hydrolase enzyme is an esterase is described. In another embodiment, the embodiment of any of the preceding embodiments wherein the esterase is a pig liver esterase is described.

In an illustrative example, a solution of compound 4 in dimethyl sulfoxide (DMSO) is added over a period of 90 hours, to a buffered solution of pig liver esterase. In another illustrative example, the buffer is a phosphate buffer. In another illustrative example, the solution of the enzyme has a pH of 6.5 to 8.5. In another illustrative, example the solution of the enzyme has a pH of 7.4 to 7.8. It is appreciated that the buffering material used can be any buffer compatible with the hydrolase enzyme used to remove the ester.

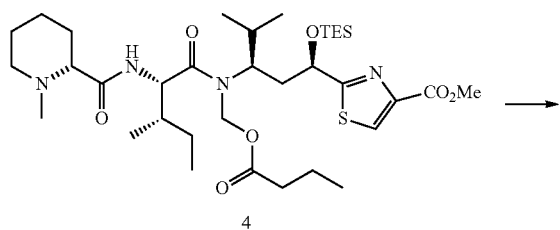

4

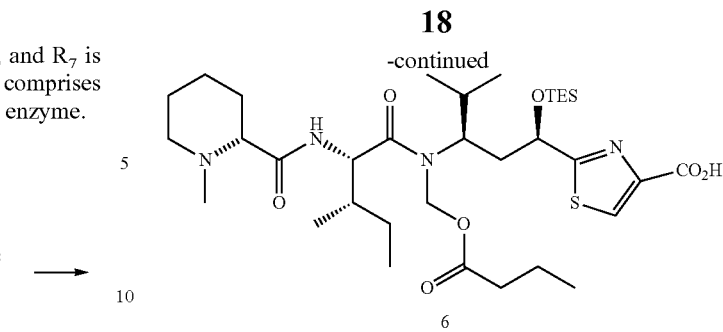

6

In another embodiment, a process is described for preparing a compound of formula G, wherein $R_5$ and $R_6$ are each independently selected from the group consisting of optionally substituted alkyl and optionally substituted cycloalkyl; $R_2$ is selected from the group consisting of optionally substituted alkyl and optionally substituted cycloalkyl; and $R_7$ is optionally substituted alkyl; wherein the process comprises the step of treating the silyl ether of compound F with a non-basic fluoride reagent. It has been discovered herein that use of basic conditions can lead to the production of a by-product arising from the rearrangement of the ester group to give compound G'.

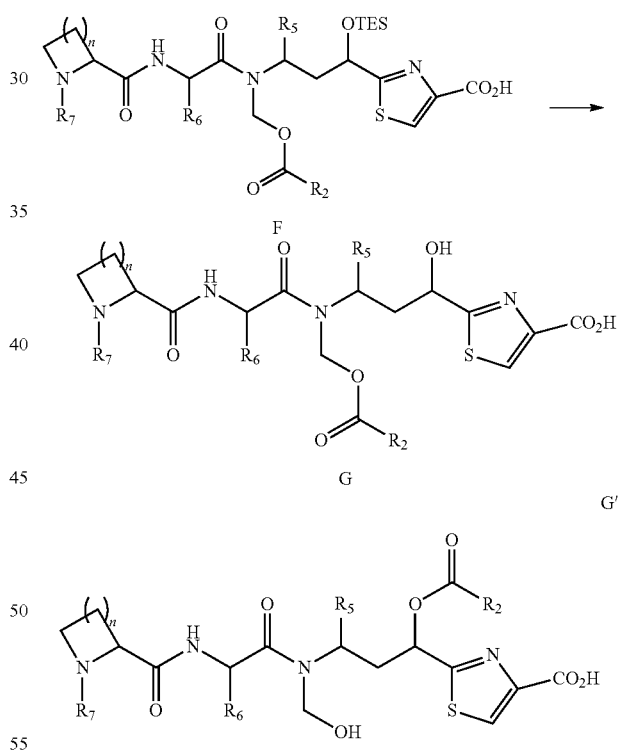

G

G'

In an illustrative example, compound 6 is treated with $Et_3N \cdot 3HF$ to cleave the TES-ether in the preparation of the corresponding alcohol 6'. It is to be understood that other non-basic fluoride reagents to cleave the silyl ether of compounds F may be used in the methods and processes described herein, including but not limited to pyridine.HF, and the like to cleave the TES-ether.

In another embodiment, a process is described for preparing a compound of formula H, wherein $R_5$ and $R_6$ are each independently selected from the group consisting of optionally substituted alkyl and optionally substituted cycloalkyl;

R₂ and R₄ are independently selected from the group consisting of optionally substituted alkyl and optionally substituted cycloalkyl; and R₇ is optionally substituted alkyl; wherein the process comprises the step of treating a compound of formula G with an acylating agent of formula R₄C(O)X₂, where X₂ is a leaving group. It is appreciated that the resulting product may contain varying amounts of the mixed anhydride of compound H and R₄CO₂H. In another embodiment, the process described in the preceding embodiment further comprises the step of treating the reaction product with water to prepare H, free of or substantially free of anhydride. In another embodiment, the process of the preceding embodiments wherein X₂ is R₄CO₂, is described. In another embodiment, the process of any one of the preceding embodiments wherein R₄ is C1-C4 alkyl is described. In another alternative of the foregoing embodiments, and each additional embodiment described herein, R₄ is methyl. In another embodiment, the process of any one of the preceding embodiments wherein R₆ is sec-butyl is described. In another embodiment, the process of any one of the preceding embodiments wherein R₇ is methyl is described. In another embodiment, the process of any one of the preceding embodiments wherein R₅ is isopropyl is described.

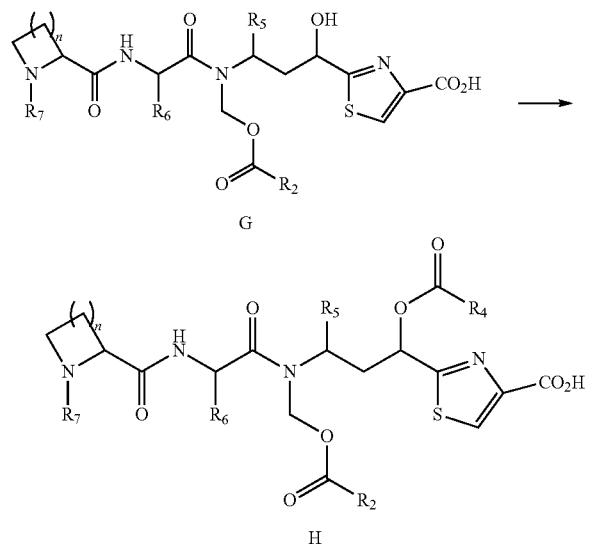

In an illustrative example, compound 6' is treated with acetic anhydride in pyridine. It has been discovered herein that shortening the time for this step of the process improves the yield of compound H by limiting the amount of the previously undescribed alternative acylation side products, such as formula 7a that are formed. It is appreciated that the resulting product may contain varying amounts of the mixed anhydride of 7 and acetic acid. In another embodiment, treatment of the reaction product resulting from the preceding step with water in dioxane yields compound 7, free of or substantially free of anhydride. It is to be understood that other solvents can be substituted for dioxane in the hydrolysis of the intermediate mixed anhydride. Alternatively, the step may be performed without solvent.

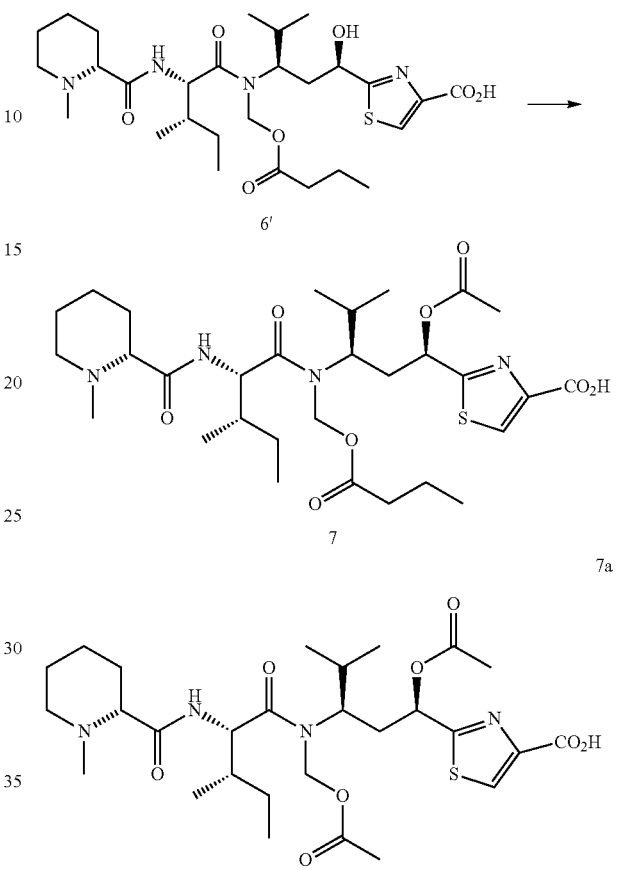

In another embodiment, a process is described for preparing a tubulysin T, wherein Ar₁ is optionally substituted aryl; R₁ is hydrogen, alkyl, arylalkyl or a pro-drug forming group; R₅ and R₆ are each independently selected from the group consisting of optionally substituted alkyl and optionally substituted cycloalkyl; R₃ is optionally substituted alkyl; R₂ and R₄ are independently selected from the group consisting of optionally substituted alkyl and optionally substituted cycloalkyl; and R₇ is optionally substituted alkyl; wherein the process comprises the steps of c) forming an active ester intermediate from a compound of formula H; and d) reacting the active ester intermediate with a compound of the formula I.

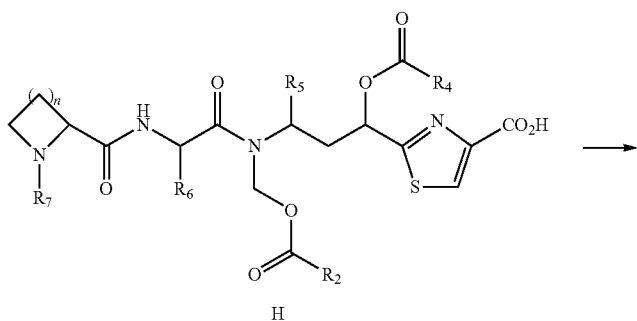

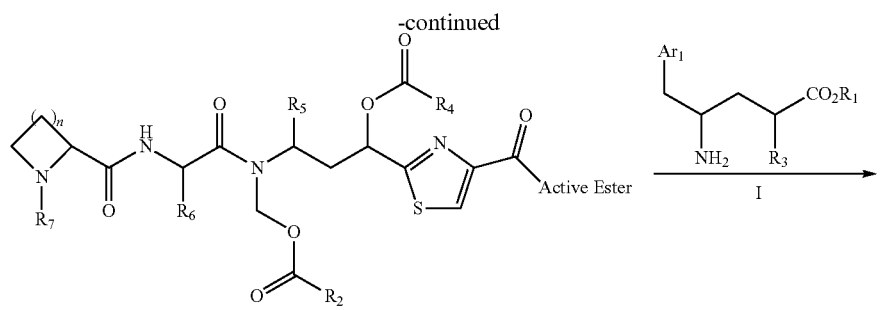

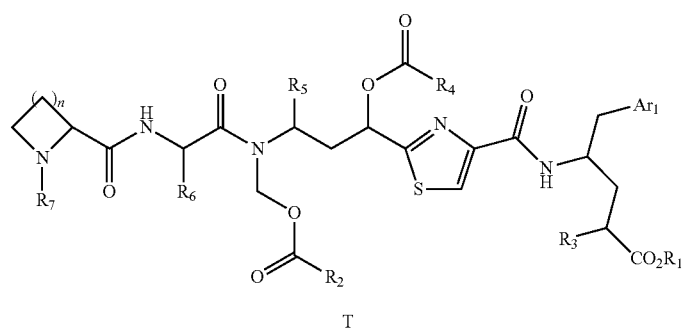

It has been discovered herein that when the free acid of I (where $R_1$ is hydrogen) is used in this step as reported previously, the desired product T can react with additional amino acid I to form poly amino acid side-products containing multiple copies of the amino acid I in a side reaction not previously reported. It has also been discovered herein that removal of excess activate ester forming agent prior to addition of the compound I, lessens or eliminates this side reaction to acceptable levels. In one embodiment, compound H is treated with an excess amount of active ester forming agent and pentafluorophenol to form the pentafluorophenol ester of compound H, followed by removal of the excess active ester forming agent prior to the addition of compound I. In another alternative of the foregoing embodiments, and each additional embodiment described herein, $Ar_1$ is phenyl. In another alternative of the foregoing embodiments, and each additional embodiment described herein, $Ar_1$ is substituted phenyl. In another alternative of the foregoing embodiments, and each additional embodiment described herein, $Ar_1$ is 4-substituted phenyl. In another alternative of the foregoing embodiments, and each additional embodiment described herein, $Ar_1$ is $R_4$-substituted phenyl. In another alternative of the foregoing embodiments, and each additional embodiment described herein, $Ar_1$ is 4-hydroxyphenyl, or a hydroxyl protected form thereof. In another alternative of the foregoing embodiments, and each additional embodiment described herein, $R_3$ is methyl. In another alternative of the foregoing embodiments, and each additional embodiment described herein, $R_1$ is hydrogen.

In an illustrative example, compound 7 is treated with an excess amount of a polymeric version of a carbodiimide and pentafluorophenol to form the pentafluorophenyl ester of 7, the polymeric carbodiimide is removed by filtration; and amino acid (S)-tubutyrosine is added to the solution to yield tubulysin B. In another embodiment, the process of any one of the preceding embodiments wherein the polymeric carbodiimide is polystyrene-$CH_2$—N=C=N-cyclohexane (PS-DCC) is described.

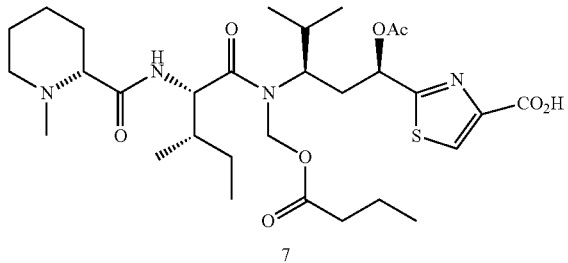

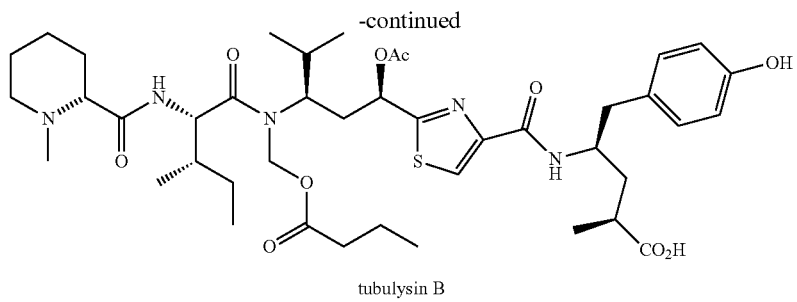

tubulysin B

In another embodiment, a compound having formula D, wherein the compound is free of or substantially free of a compound having formula C-1 is described, where in $R_2$, $R_5$, $R_6$, $R_7$, and $R_8$ are as described in any of the embodiments described herein. Without being bound by theory, it is believed herein that compounds C-1 are formed from the corresponding compounds C via an acyl transfer.

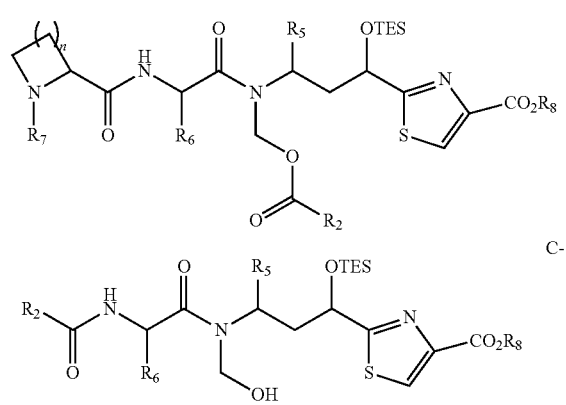

D

C-1

In another embodiment, compound 4, free of or substantially free of compound 8 and/or compound 9 is described. In another embodiment, an optically pure form of compound 4 is formed.

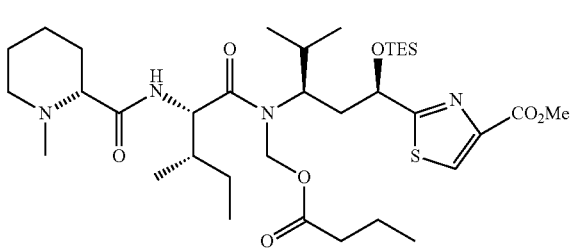

4

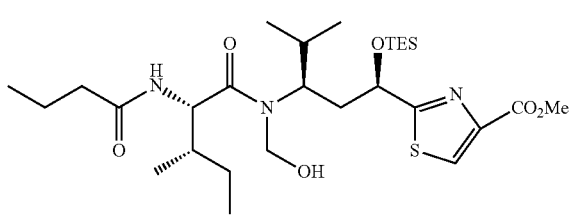

8

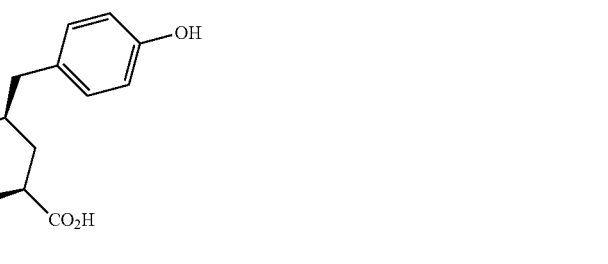

9

In another embodiment, a compound H, wherein the compound H is free of or substantially free, of a compound having the formula Oxazine-2 is described.

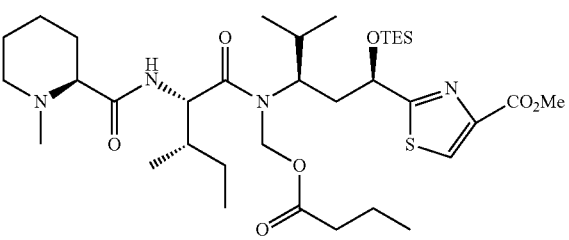

H

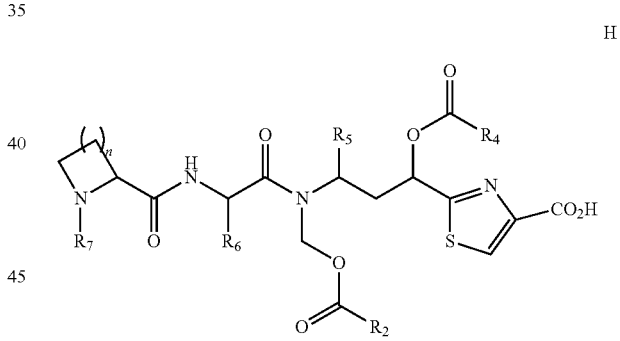

Oxazine-2

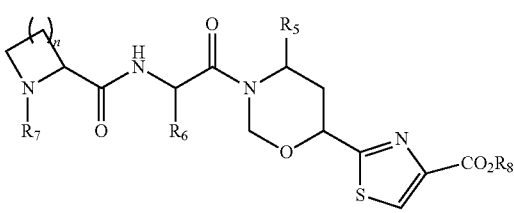

In another embodiment, a compound F is described wherein $R_2$, $R_5$, $R_6$, $R_7$ and $R_8$ are as described in the any of the embodiments described herein.

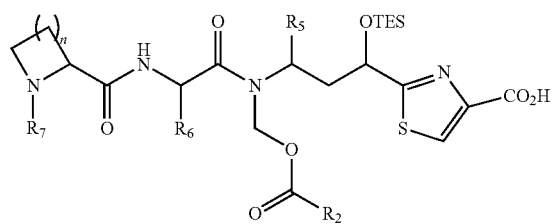

F

In another embodiment, the compound having formula 6 is described.

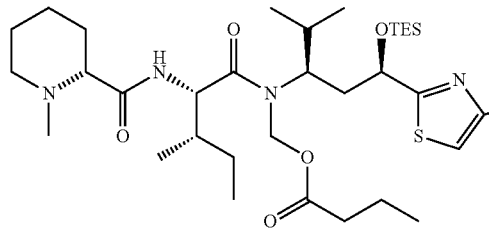

6

In another embodiment a compound G, where the compound is free of or substantially free of a compound G' is described, wherein $R_2$, $R_5$, $R_6$, and $R_7$ are as described in any of the embodiments described herein.

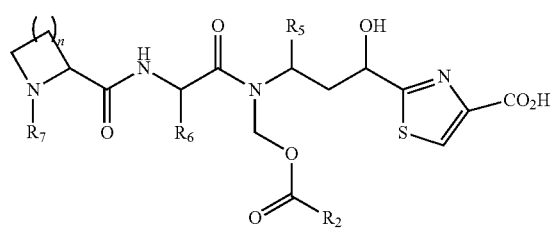

G

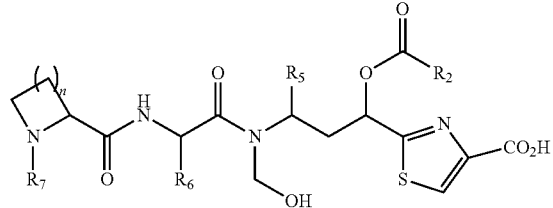

G'

In another embodiment, compound 6' is described, wherein compound 6' is free of or substantially free of the isomer of G' shown below

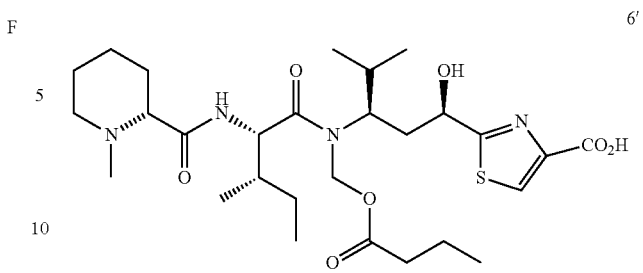

6'

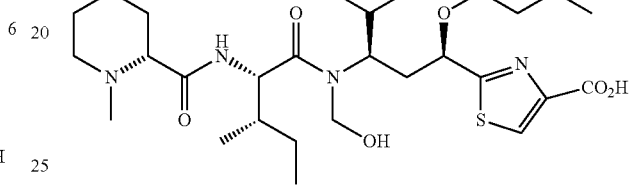

isomer of 6'

In another embodiment, compound 7 is described, wherein compound 7 is free of or substantially free of compound 7a is described

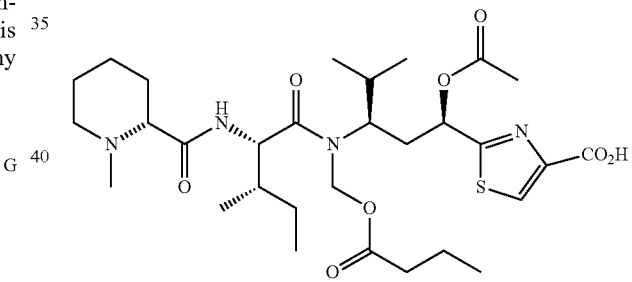

7

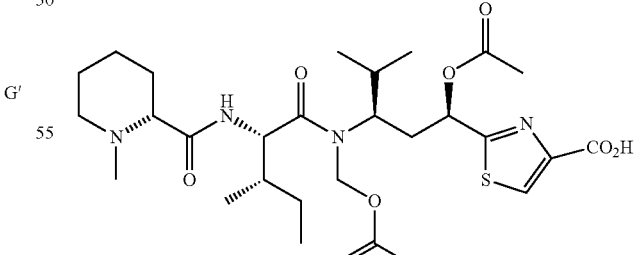

7a

In another embodiment, a compound H is described wherein $R_4$ is Me and $R_2$, $R_5$, $R_6$, and $R_7$ are as described in any of the embodiments described herein; and the compound H is free of or substantially free of the compound H wherein $R_4$ and $R_2$ are both Me.

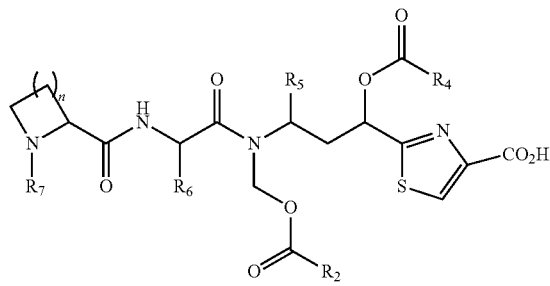

In another alternative of the foregoing embodiments, and each additional embodiment described herein, $R_5$ is isopropyl.

In another alternative of the foregoing embodiments, and each additional embodiment described herein, $R_6$ is sec-butyl.

In another alternative of the foregoing embodiments, and each additional embodiment described herein, $R_8$ is methyl.

In another alternative of the foregoing embodiments, and each additional embodiment described herein, $R_2$ is $CH_2CH(CH_3)_2$, $CH_2CH_2CH_3$, $CH_2CH_3$, $CH=C(CH_3)_2$, or $CH_3$.

In another alternative of the foregoing embodiments, and each additional embodiment described herein, n is 3.

In another alternative of the foregoing embodiments, and each additional embodiment described herein, $R_7$ is methyl.

In another alternative of the foregoing embodiments, and each additional embodiment described herein, $R_8$ is methyl.

In another alternative of the foregoing embodiments, and each additional embodiment described herein, $R_4$ is methyl.

In another alternative of the foregoing embodiments, and each additional embodiment described herein, $Ar_1$ is phenyl. In another alternative of the foregoing embodiments, and each additional embodiment described herein, $Ar_1$ is substituted phenyl. In another alternative of the foregoing embodiments, and each additional embodiment described herein, $Ar_1$ is 4-substituted phenyl. In another alternative of the foregoing embodiments, and each additional embodiment described herein, $Ar_1$ is $R_A$-substituted phenyl. In another alternative of the foregoing embodiments, and each additional embodiment described herein, $Ar_1$ is 4-hydroxyphenyl, or a hydroxyl protected form thereof.

In another alternative of the foregoing embodiments, and each additional embodiment described herein, $R_3$ is methyl.

In another alternative of the foregoing embodiments, and each additional embodiment described herein, $R_1$ is hydrogen.

Illustrative embodiments of the invention are further described by the following enumerated clauses: 1. A process for preparing a compound of the formula

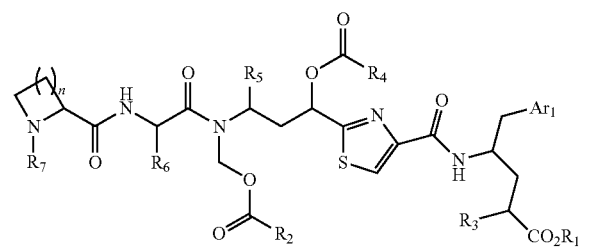

or a pharmaceutically acceptable salt thereof; wherein $Ar_1$ is optionally substituted aryl; $R_1$ is hydrogen, alkyl, arylalkyl or a pro-drug forming group; $R_2$ is selected from the group consisting of optionally substituted alkyl and optionally substituted cycloalkyl; $R_3$ is optionally substituted alkyl; $R_4$ is optionally substituted alkyl or optionally substituted cycloalkyl; $R_5$ and $R_6$ are each independently selected from the group consisting of optionally substituted alkyl and optionally substituted cycloalkyl; $R_7$ is optionally substituted alkyl; and n is 1, 2, 3, or 4; wherein the process comprises the step of treating a compound of formula A with triethylsilyl chloride and imidazole in an aprotic solvent, where $R_8$ is C1-C6 unbranched alkyl

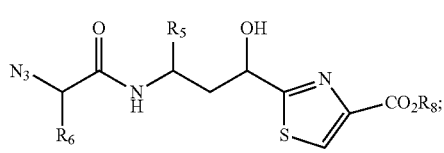

or the step of treating a compound of formula B with a base and a compound of the formula $ClCH_2OC(O)R_2$ in an aprotic solvent at a temperature from about −78° C. to about 0° C.; wherein the molar ratio of the compound of the formula $ClCH_2OC(O)R_2$ to the compound of formula B from about 1 to about 1.5, where $R_8$ is C1-C6 unbranched alkyl

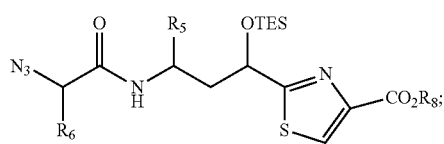

or the steps of a) preparing a compound of formula (E1), where $X_1$ is a leaving group, from a compound of formula E

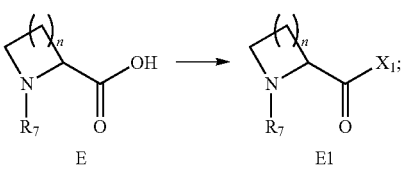

and b) treating a compound of formula C under reducing conditions in the presence of the compound of formula E1, where $R_8$ is C1-C6 unbranched alkyl

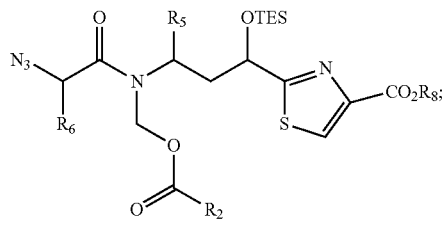

or the step of treating compound D with a hydrolase enzyme, where $R_8$ is C1-C6 unbranched alkyl

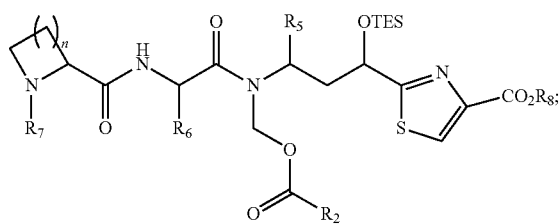
D or the step of treating the silyl ether of compound F with a non-basic fluoride reagent

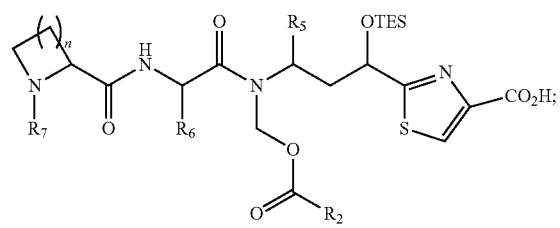
F or the step of treating a compound of formula G with an acylating agent of formula $R_4C(O)X_2$, where $X_2$ is a leaving group

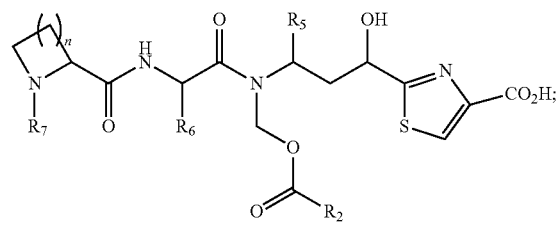
G or the steps of c) forming an active ester intermediate from a compound of formula H

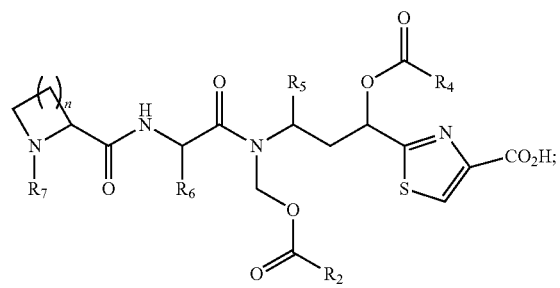
H and d) reacting the active ester intermediate with a compound of the formula I

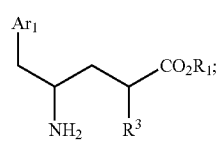

or combinations thereof. 1a. The process of clause 1 wherein $R_4$ is optionally substituted alkyl. 2. The process of clause 1 or 1a comprising the step of treating a compound of formula A with triethylsilyl chloride and imidazole in an aprotic solvent, where $R_8$ is C1-C6 unbranched alkyl

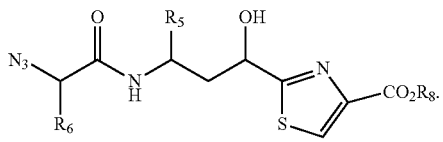
A

3. The process of clause 1 or 1a comprising the step of treating a compound of formula B with a base and a compound of the formula $ClCH_2OC(O)R_2$ in an aprotic solvent at a temperature from about −78° C. to about 0° C.; wherein the molar ratio of the compound of the formula $ClCH_2OC(O)R_2$ to the compound of formula B from about 1 to about 1.5, where $R_8$ is C1-C6 unbranched alkyl B
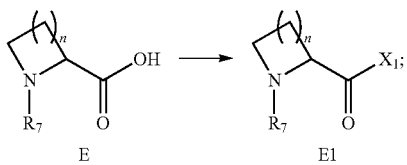

4. The process of clause 1 or 1a comprising the steps of a) preparing a compound of formula (E1), where $X_1$ is a leaving group, from a compound of formula E

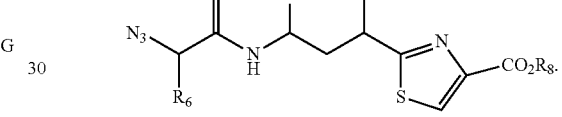

and b) treating a compound of formula C under reducing conditions in the presence of the compound of formula E1, where $R_8$ is C1-C6 unbranched alkyl C
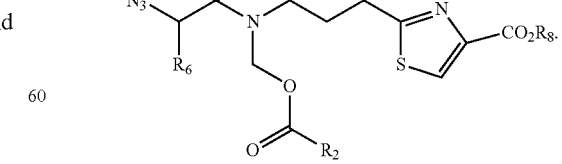

5. The process of clause 1 or 1a comprising the step of treating compound D with a hydrolase enzyme, where $R_8$ is C1-C6 unbranched alkyl

D

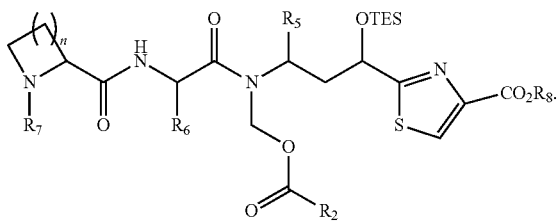

6. The process of clause 1 or 1a comprising the step of treating a compound of formula G with an acylating agent of formula $R_4C(O)X_2$, where $X_2$ is a leaving group

G

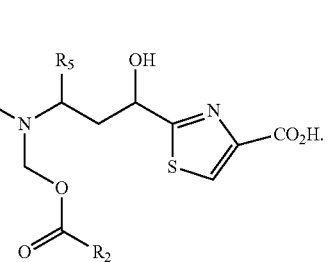

7. The process of clause 1 or 1a comprising the steps of c) forming an active ester intermediate from a compound of formula H

H

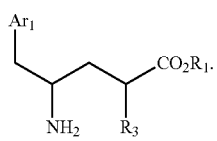

and d) reacting the active ester intermediate with a compound of the formula I

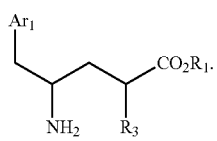

8. The process of any one of clauses 1 to 7 or 1a wherein $R_1$ is hydrogen, benzyl, or C1-C4 alkyl. 9. The process of any one of the preceding clauses wherein $R_1$ is hydrogen. 10. The process of any one of the preceding clauses wherein $R_2$ is C1-C8 alkyl or C3-C8 cycloalkyl. 11. The process of any one of the preceding clauses wherein $R_2$ is n-butyl. 12. The process of any one of the preceding clauses wherein $R_3$ is C1-C4 alkyl. 13. The process of any one of the preceding clauses wherein $R_3$ is methyl. 14. The process of any one of the preceding clauses wherein $Ar_1$ is phenyl or hydroxyphenyl. 15. The process of any one of the preceding clauses wherein $Ar_1$ is 4-hydroxyphenyl. 16. The process of any one of the preceding clauses wherein $R_4$ is C1-C8 alkyl or C3-C8 cycloalkyl. 17. The process of any one of the preceding clauses wherein $R_4$ is methyl. 18. The process of any one of the preceding clauses wherein $R_5$ is branched C3-C6 or C3-C8 cycloalkyl. 19. The process of any one of the preceding clauses wherein $R_5$ is iso-propyl. 20. The process of any one of the preceding clauses wherein $R_6$ is branched C3-C6 or C3-C8 cycloalkyl. 21. The process of any one of the preceding clauses wherein $R_5$ is sec-butyl. 22. The process of any one of the preceding clauses wherein $R_7$ is C1-C6 alkyl. 23. The process of any one of the preceding clauses wherein $R_7$ is methyl. 24. The process of any one of the preceding clauses wherein $R_2$ is $CH_2CH(CH_3)_2$, $CH_2CH_2CH_3$, $CH_2CH_3$, $CH=C(CH_3)_2$, or $CH_3$. 25. The process of any one of the preceding clauses wherein $Ar_1$ is substituted phenyl. 26. The process of any one of the preceding clauses wherein $Ar_1$ is 4-substituted phenyl. 27. The process of any one of the preceding clauses wherein $Ar_1$ is $R_4$-substituted phenyl. 28. The process of any one of the preceding clauses wherein $Ar_1$ is 4-hydroxyphenyl, or a hydroxyl protected form thereof.

It is to be understood that as used herein, the term tubulysin refers both collectively and individually to the naturally occurring tubulysins, and the analogs and derivatives of tubulysins. Illustrative examples of a tubulysin are shown in Table 1.

As used herein, the term tubulysin generally refers to the compounds described herein and analogs and derivatives thereof. It is also to be understood that in each of the foregoing, any corresponding pharmaceutically acceptable salt is also included in the illustrative embodiments described herein.

It is to be understood that such derivatives may include prodrugs of the compounds described herein, compounds described herein that include one or more protection or protecting groups, including compounds that are used in the preparation of other compounds described herein.

In addition, as used herein the term tubulysin also refers to prodrug derivatives of the compounds described herein, and including prodrugs of the various analogs and derivatives thereof. In addition, as used herein, the term tubulysin refers to both the amorphous as well as any and all morphological forms of each of the compounds described herein. In addition, as used herein, the term tubulysin refers to any and all hydrates, or other solvates, of the compounds described herein.

It is to be understood that each of the foregoing embodiments may be combined in chemically relevant ways to generate subsets of the embodiments described herein. Accordingly, it is to be further understood that all such subsets are also illustrative embodiments of the invention described herein.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, (E)-, and (Z)-double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term aprotic solvent refers to a solvent which does not yield a proton to the solute(s) under reaction conditions. Illustrative examples of nonprotic solvents are tetrahydrofuran (THF), 2,5-dimethyl-tetrahydrofuran, 2-methyl-tetrahydrofuran, tetrahydropyran, diethyl ether, t-butyl methyl ether, dimethyl formamide, N-methylpyrrolidinone (NMP), and the like. It is appreciated that mixtures of these solvents may also be used in the processes described herein.

As used herein, an equivalent amount of a reagent refers to the theoretical amount of the reagent necessary to transform a starting material into a desired product, i.e. if 1 mole of reagent is theoretically required to transform 1 mole of the starting material into 1 mole of product, then 1 equivalent of the reagent represents 1 mole of the reagent; if X moles of reagent are theoretically required to convert 1 mole of the starting material into 1 mole of product, then 1 equivalent of reagent represents X moles of reagent.

As used herein, the term active ester forming agent generally refers to any reagent or combinations of reagents that may be used to convert a carboxylic acid into an active ester.

As used herein, the term active ester generally refers to a carboxylic acid ester compound wherein the divalent oxygen portion of the ester is a leaving group resulting in an ester that is activated for reacting with compounds containing functional groups, such as amines, alcohols or sulfhydryl groups. Illustrative examples of active ester-forming compounds are N-hydroxysuccinimide, N-hydroxyphthalimide, phenols substituted with electron withdrawing groups, such as but not limited to 4-nitrophenol, pentafluorophenol, N,N'-disubstituted isoureas, substituted hydroxyheteroaryls, such as but not limited to 2-pyridinols, 1-hydroxybenzotriazoles, 1-hydroxy-7-aza-benzotriazoles, cyanomethanol, and the like. Illustratively, the reaction conditions for displacing the active ester with a compound having an amino, hydroxy or thiol group are mild. Illustratively, the reaction conditions for displacing the active ester with a compound having an amino, hydroxy or thiol group are performed at ambient or below ambient temperatures. Illustratively, the reaction conditions for displacing the active ester with a compound having an amino, hydroxy or thiol group are performed without the addition of a strong base. Illustratively, the reaction conditions for displacing the active ester with a compound having an amino, hydroxy or thiol group are performed with the addition of a tertiary amine base, such as a tertiary amine base having a conjugate acid pKa of about 11 or less, about 10.5 or less, and the like.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic groups, including aromatic carbocyclic and aromatic heterocyclic groups, each of which may be optionally substituted. As used herein, the term "carbaryl" includes aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, acylcarbonyl, and the like, each of which is optionally substituted.

As used herein, the term "carboxylate and derivatives thereof" includes the group $CO_2H$ and salts thereof, and esters and amides thereof, and CN.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

As used herein, the term "optionally substituted aryl" includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

Illustrative substituents include, but are not limited to, a radical $—(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, $(C_1$-$C_6$ alkyl)($C_1$-$C_6$ alkyl)amino, alkylcarbonylamino, N—$(C_1$-$C_6$ alkyl)alkylcarbonylamino, aminoalkyl, $C_1$-$C_6$ alkylaminoalkyl, $(C_1$-$C_6$ alkyl)($C_1$-$C_6$ alkyl)aminoalkyl, alkylcarbonylaminoalkyl, N—$(C_1$-$C_6$ alkyl)alkylcarbonylaminoalkyl, cyano, and nitro; or $Z^X$ is selected from $—CO_2R^4$ and $—CONR^5R^6$, where $R^4$, $R^5$, and $R^6$ are each independently selected in each occurrence from hydrogen, $C_1$-$C_6$ alkyl, and aryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, $(C_3-C_{20})$alkanoyl; halo-$(C_3-C_{20})$alkanoyl; $(C_3-C_{20})$alkenoyl; $(C_4-C_7)$cycloalkanoyl; $(C_3-C_6)$-cycloalkyl$(C_2-C_{16})$alkanoyl; optionally substituted aroyl, such as unsubstituted aroyl or aroyl substituted by 1 to 3 substituents selected from the group consisting of halogen, cyano, trifluoromethanesulphonyloxy, $(C_1-C_3)$alkyl and $(C_1-C_3)$alkoxy, each of which is optionally further substituted with one or more of 1 to 3 halogen atoms; optionally substituted aryl$(C_2-C_{16})$alkanoyl, such as the aryl radical being unsubstituted or substituted by 1 to 3 substituents selected from the group consisting of halogen, $(C_1-C_3)$alkyl and $(C_1-C_3)$alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1-C_3)$alkyl, and $(C_1-C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

As used herein, the term "treating", "contacting" or "reacting" when referring to a chemical reaction means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, $(21^{st}$ ed., 2005)).

EXAMPLES

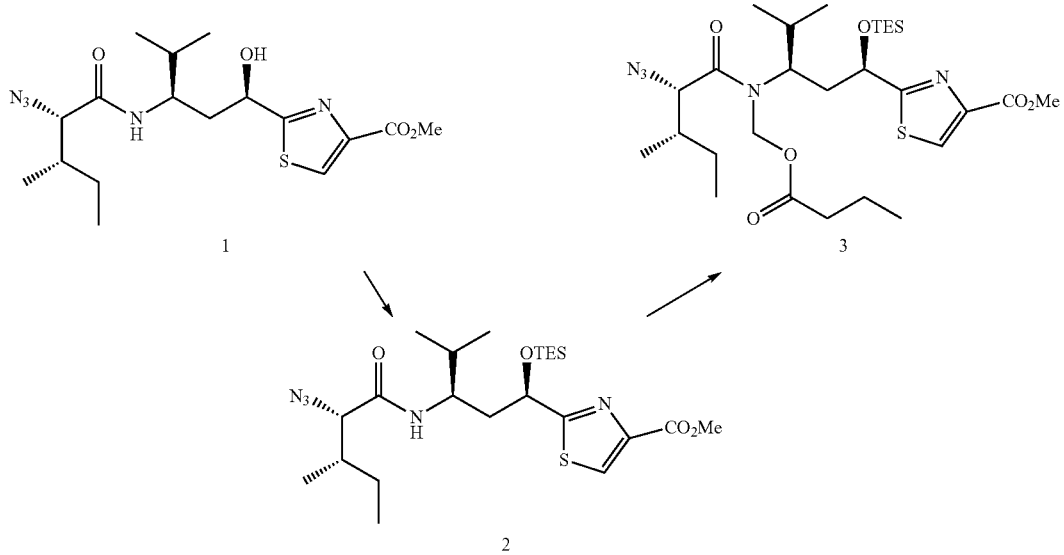

Synthesis of Dipeptide 3.

4.9 g of dipeptide 1 (11.6 mmol) was dissolved in 60 mL dichloromethane, imidazole (0.87 g, 12.7 mmol) was added to the resulting solution at 0° C. The reaction mixture was warmed slightly to dissolve all solids and re-cooled to 0° C. TESCl (2.02 mL, 12.1 mmol) was added drop-wise at 0° C., the reaction mixture was stirred under argon and warmed to room temperature over 2 h. TLC (3:1 hexanes/EtOAc) showed complete conversion. The reaction was filtered to remove the imidazole HCl salt, extracted with de-ionized water, and the aqueous phase was back-washed with dichloromethane, the combined organic phase was washed with brine, dried over $Na_2SO_4$, filtered to remove the $Na_2SO_4$, concentrated under reduced pressure, co-evaporated with toluene and dried under high-vacuum overnight to give 6.4 g of crude product 2 (vs 5.9 g of theoretical yield).

The crude product 2 was co-evaporated with toluene again and used without further purification. TES protected dipeptide was dissolved in 38 mL THF (anhydrous, inhibitor-free) and cooled to −45° C. and stirred for 15 minutes before adding KHMDS (0.5 M in toluene, 25.5 mL, 12.8 mmol, 1.1 equiv) drop-wise. After the addition of KHMDS was complete, the reaction mixture was stirred at −45° C. for 15 minutes, and chloromethyl butyrate (1.8 mL, 1.2 equiv, 14 mmol) was added. The reaction mixture changed from light yellow to a blueish color. TLC (20% EtOAc/petroleum ether) showed the majority of starting material was converted. LC-MS showed about 7% starting material left. The reaction was quenched by adding 3 mL MeOH, the mixture was warmed to room temperature and concentrated under reduced pressure to an oily residue. The residue was dissolved in petroleum ether and passed through short silica plug to remove the potassium salt. The plug was washed with 13% EtOAc/petroleum ether, and the collected eluates were combined and concentrated under reduced pressure. The crude alkylated product was passed through an additional silica plug (product/silica=1:50) and eluted with 13% EtOAc/petroleum ether to remove residual starting material to give 5.7 g of product 3 (two steps, yield 76%)

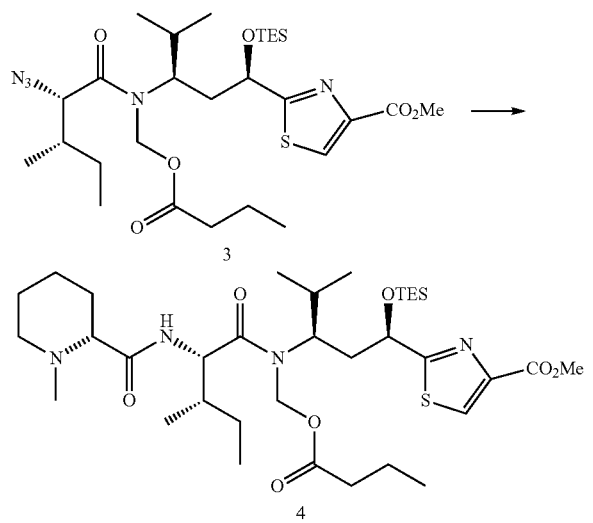

Synthesis of Tripeptide 4.

Alkylated dipeptide 3 (4.3 g, 7.0 mmol), N-methyl pipecolinate (MEP) (4.0 g, 28.0 mmol, 4 equiv) and pentafluorophenol (5.7 g, 30.8 mmol. 4.4 equiv) were added to a flask. N-methyl pyrrolidone (NMP, 86 mL) was added to the mixture. To the mixture was added diisopropylcarbodiimide (DIC, 4.77 mL, 30.8 mmol, 4.4 equiv) was added to the mixture. The mixture was stirred at room temperature for 1 h. Pd/C (10%, dry, 1.7 g) was added. The flask was shaken under hydrogen (30-35 psi) for 5 hours. The reaction mixture was analyzed by HPLC. The starting material was found to be less than 3%. The mixture was filtered through diatomaceous earth. The diatomaceous earth was extracted with 200 mL ethyl acetate. The filtrate and the ethyl acetate extract were combined and transferred to a separatory funnel and washed with 1% $NaHCO_3$/10% NaCl solution (200 mL×4). The organic layer was isolated and evaporated on a rotary evaporator under reduced pressure. The crude product was dissolved in 40 mL of $MeOH/H_2O$ (3:1). The crude product solution was loaded onto a Biotage C18 column (Flash 65i, 350 g, 450 mL, 65×200 mm) and eluted with buffer A [10 mM $NH_4OAc$/ACN (1:1)] and B (ACN, acetonitrile). The fractions were collected and organic solvent was removed by evaporating on a rotary evaporator. 100 mL of 10% NaCl solution and 100 mL of methyl tert-butyl ether (MTBE) were added to the flask and the mixture was transferred to a separatory funnel. The organic layer was isolated and dried over anhydrous $Na_2SO_4$, filtered and evaporated on a rotary evaporator to dryness. 2.5 g of tripeptide intermediate 4 was obtained (yield 50%).

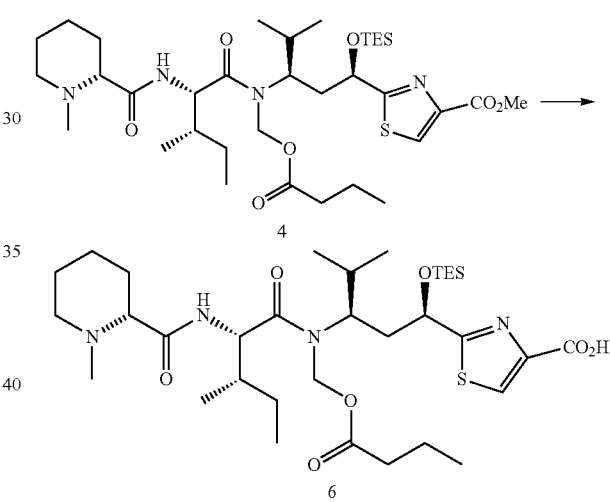

Synthesis of Tripeptide Acid 6.

To 2 L of 0.05 M phosphate (pH=7.4) at 30° C. was added 3.6 g of porcine liver esterase (17 units/mg). 3.0 g of methyl ester 4 was dissolved in 100 mL of DMSO. The first 50 mL of this solution was added at a rate of 1.1 mL/h, and the second half was added at a rate of 1.2 mL/h via syringe pump. After the addition was complete, the reaction mixture was allowed to stir at 30° C. for several hours. HPLC of an EtOAc extract of the reaction mixture showed the reaction was complete. The reaction mixture was drained from the reactor in 1 L portions and extracted with EtOAc (3×1 L). The combined extracts were washed with brine, dried over $Mg_2SO_4$ and concentrated under reduced pressure. 2.8 g of product 6 was recovered (95%). The product appeared to be clean by UPLC analysis, except for pentafluorophenol carried over from the previous reaction.

Intermediate 6 spectral data: LCMS (ESI) $[M+H]^+$ 697.3; $^1$H NMR (CD3OD) 8.02 (s, 1 H), 5.94 (d, J=12.3 Hz, 1 H), 5.48 (d, J=12.3 Hz, 1 H), 4.93 (d, J=8.2 Hz, 1 H), 4.65 (d, J=8.5 Hz, 1 H), 3.63 (s, br, 1 H), 2.91 (br, 1 H), 2.67 (s, 3 H), 2.53-2.14 (m, 3 H), 2.14-1.94 (m, 4 H), 1.94-1.74 (m, 4 H), 1.74-1.50 (m, 4 H), 1.28-1.17 (m, 1 H), 1.02-0.83 (m, 24 H), 0.71-0.55 (m, 6 H).

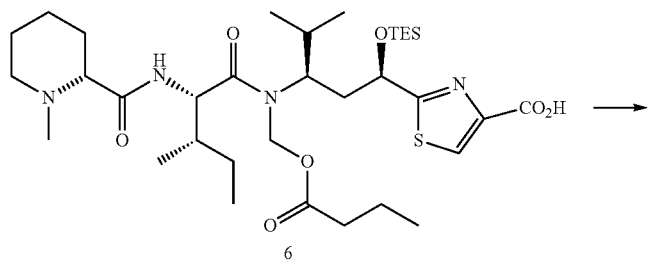

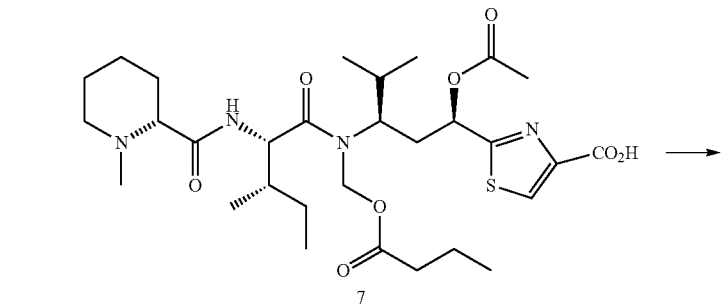

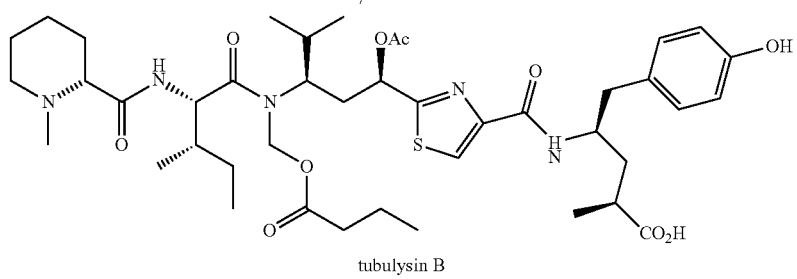

tubulysin B

Synthesis of Tubulysin B.

1.4 g (2.01 mmol) of tripeptide 6 was dissolved in 8.4 mL THF and 327.4 µL (2.01 mmol) of 3HF.NEt$_3$ was added and the reaction mixture stirred for 30 minutes. LC-MS analysis (10% to 100% acetonitrile, pH 7 buffer) confirmed complete deprotection of the TES group. THF was removed under reduced pressure. The residue was dried under high vacuum for 5 minutes. The crude product was dissolved in 8.4 mL dry pyridine. 2.85 mL (30.15 mmol, 15 equiv) of Ac$_2$O was added at 0° C. The resulting clear solution was stirred at room temperature for 3.5 hours. LC-MS analysis (10% to 100% acetonitrile, pH 7.0) indicated >98% conversion. 56 mL of dioxane/H$_2$O was added and the resulting mixture stirred at room temperature for 1 hour. The mixture was concentrated under reduced pressure. The residue was co-evaporated with toluene (3×) and dried under high vacuum overnight. Crude product 7 was used directly for the next reaction.

Intermediate 7 spectral data: LCMS (ESI) [M+H]$^+$ 625.2; $^1$H NMR (CD3OD) 8.00 (s, 1 H), 6.00(s, br, 1 H), 5.84 (d, J=12.1 Hz, 1 H), 5.40 (d, J=12.1 Hz, 1 H), 4.63(d, J=9.1 Hz, 1 H), 3.09 (br, 1 H), 2.60-2.20 (m, 7 H), 2.12 (s, 3 H), 2.09-1.86 (m, 3 H), 1.80-1.63 (m, 3 H), 1.59(m, 5 H), 1.19 (m, 1 H), 1.03-0.81 (m, 15 H); $^{13}$C NMR (CD3OD) 176.2, 174.2, 172.1, 169.1, 155.5, 125.2, 71.4, 69.6, 56.6, 55.5, 44.3, 37.7, 37.1, 36.4, 32.0, 31.2, 25.6, 23.7, 21.0, 20.9, 20.7, 19.3, 16.5, 14.2, 11.0

Method A. The crude tripeptide acid 7 was dissolved in 28 mL EtOAc (anhydrous) and 740 mg (4.02 mmol, 2.0 equiv) of pentafluorophenol was added, followed by 1.04 g (5.03 mmol, 2.5 equiv) of DCC. The resulting reaction mixture was stirred at room temperature for 1 hour. LC-MS (5% to 80% acetonitrile, pH=2.0, formic acid) analysis indicated >95% conversion. The urea by-product was filtered off, the EtOAc was removed under reduced pressure, and the residue was dried under high vacuum for 5 minutes. The residue was dissolved in 8.4 mL DMF, and tubutyrosine hydrochloride salt (Tut-HCl, 678.7 mg, 2.61 mmol, 1.3 equiv) was added, followed by DIPEA (2.28 mL, 13.07 mmol, 6.5 equiv). The resulting clear solution was stirred at room temperature for 10 minutes. The reaction mixture was diluted with DMSO and purified on prep-HPLC (X-bridge column, 10 mM NH$_4$OAc, pH=6.3, 25% to 100% acetonitrile). Pure fractions were combined, acetonitrile was removed under reduced pressure, extracted with EtOAc (3×), and dried over Na$_2$SO$_4$. The EtOAc was removed under reduced pressure and the residue was dried under high vacuum for 1 hour to yield 513 mg of the desired product (31% combined yield from 6).

Method B. Tripeptide 7 (229 mg, 0.367 mmol) was dissolved in EtOAc (anhydrous), 134.9 mg (0.733 mmol, 2.0 equiv) of pentafluorophenol was added, followed by 970 mg (1.84 mmol, 5.0 equiv) of DCC on the resin. The resulting reaction mixture was stirred at room temperature for 16 hours. LC-MS analysis indicated >96% conversion. The reaction mixture was filtered and concentrated to dryness, dried under high vacuum for 5 minutes. The residue was dissolved in 3.5 mL DMF, Tut-HCl (123.9 mg, 0.477 mmol, 1.3 equiv) was added, followed by DIPEA (0.42 mL, 2.386 mmole, 6.5 equiv). The resulting clear solution was stirred at room temperature for 10 minutes. The reaction mixture was diluted with DMSO, purified on prep-HPLC (X-bridge column, 10 mM NH$_4$OAc, 25% to 100%, two runs). The pure fractions were combined, the acetonitrile was removed under reduced pressure, the residue was extracted with EtOAc (2×) and the combined EtOAc extracts dried over Na$_2$SO$_4$. The EtOAc was removed under reduced pressure. The residue was dried under high vacuum for 1 hour to yield 175 mg of desired product (58% combined yield from 6).

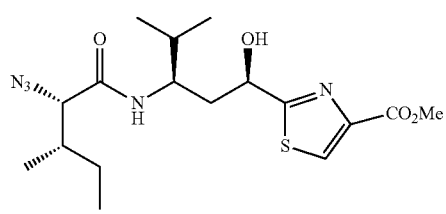

1

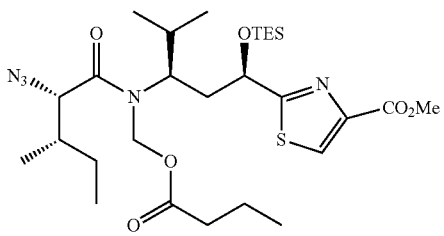

3

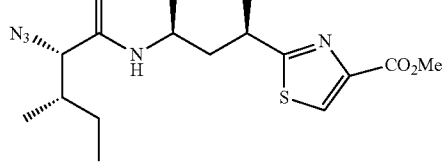

2

Large Scale Synthesis of Dipeptide 3.

10.2 g of dipeptide 1 (25.6 mmol) was dissolved in 130 mL dichloromethane, imidazole (1.9 g, 28.1 mmol) was added to the resulting solution at 0° C. The reaction mixture was warmed slightly to dissolve all solids and re-cooled to 0° C. TESCl (4.5 mL, 26.8 mmol) was added drop-wise at 0° C., the reaction mixture was stirred under argon and warmed to room temperature over 2 h. TLC (3:1 hexanes/EtOAc) showed complete conversion. The reaction was filtered to remove the imidazole HCl salt, extracted with de-ionized water, and the aqueous phase was back-washed with dichloromethane, the combined organic phase was washed with brine, dried over $Na_2SO_4$, filtered to remove the $Na_2SO_4$, concentrated under reduced pressure, co-evaporated with toluene and dried under high-vacuum overnight to give 12.2 g of product 2.

The crude product 2 was co-evaporated with toluene again and used without further purification. TES protected dipeptide was dissolved in 80 mL THF (anhydrous, inhibitor-free) and cooled to −45° C. and stirred for 15 minutes before adding KHMDS (0.5 M in toluene, 50 mL, 25.0 mmol, 1.05 equiv) drop-wise. After the addition of KHMDS was complete, the reaction mixture was stirred at −45° C. for 15 minutes, and chloromethyl butyrate (3.6 mL, 1.2 equiv, 28.3 mmol) was added. The reaction mixture changed from light yellow to a blueish color. TLC (20% EtOAc/petroleum ether) showed the reaction was complete. The reaction was quenched by adding 20 mL MeOH, the mixture was warmed to room temperature and concentrated under reduced pressure to an oily residue. The residue was dissolved in petroleum ether and passed through short silica plug to remove the potassium salt. The plug was washed with 13% EtOAc/petroleum ether, and the collected eluents were combined and concentrated under reduced pressure to give 12.1 g of product 3 (two steps, yield 76%)

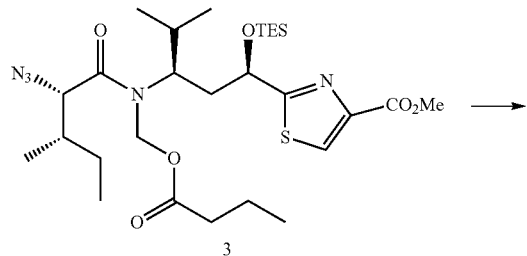

3

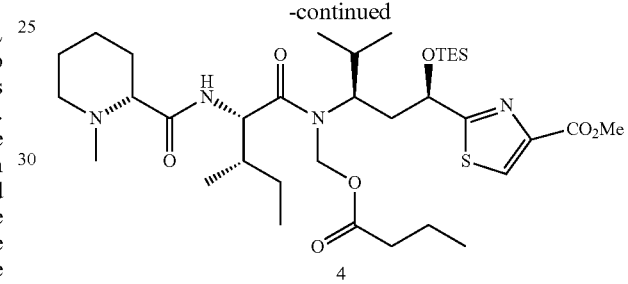

4

Large Scale Synthesis of Tripeptide 4.

Alkylated dipeptide 3 (7.6 g, 12.4 mmol), N-methyl pipecolinate (MEP) (7.0 g, 48.9 mmol, 4 equiv) and pentafluorophenol (10.0 g, 54.3 mmol. 4.4 equiv) were added to a flask. N-methyl pyrrolidone (NMP, 152 mL) was added to the mixture. To the mixture was added diisopropylcarbodiimide (DIC, 8.43 mL, 54.4 mmol, 4.4 equiv) was added to the mixture. The mixture was stirred at room temperature for 1 h. Pd/C (10%, dry, 3.0 g) was added. The flask was shaken under hydrogen (30-35 psi) for 5 hours. The reaction mixture was analyzed by HPLC. The reaction was complete. The mixture was filtered through celite. The celite was washed with 500 mL ethyl acetate. The solutions were combined and transferred to a separatory funnel and washed with 1% $NaHCO_3$/ 10% NaCl solution (250 mL×4). The organic layer was isolated and evaporated on a rotary evaporator under reduced pressure. The crude product was dissolved in dichloromethane and the urea was filtered. The crude product solution was loaded onto a Teledyne Redisep Silica Column (330 g) and purified with EtOAc/petroleum ether on CombiFlash flash chromatography system. The fractions were collected and organic solvent was removed by evaporating to give 5.0 g of the tripeptide (61%). NMR and mass spectral data were consistent with those measured for the Example

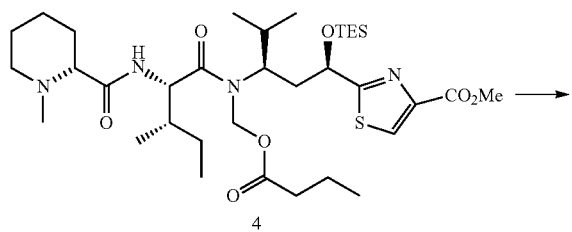

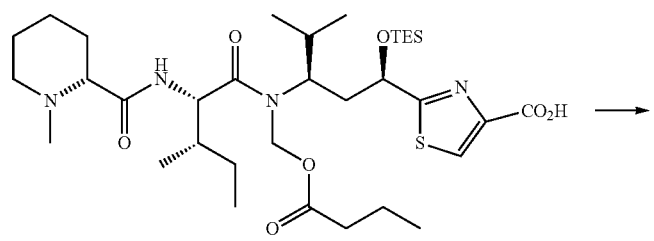

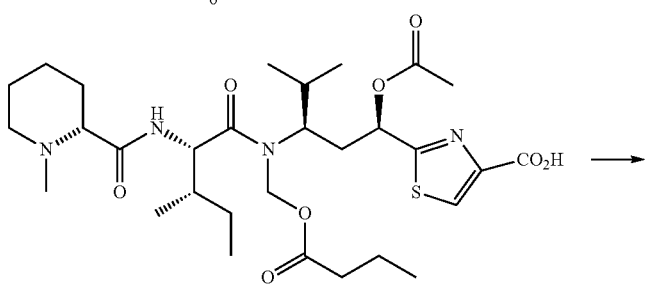

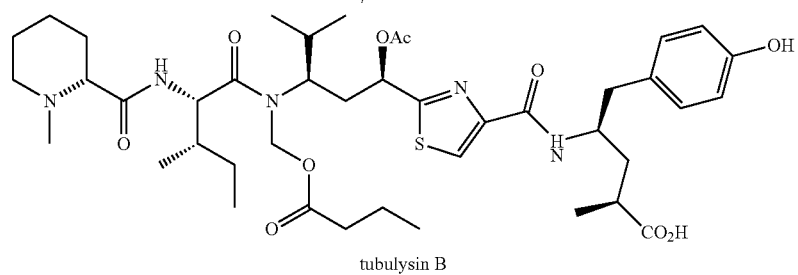

tubulysin B

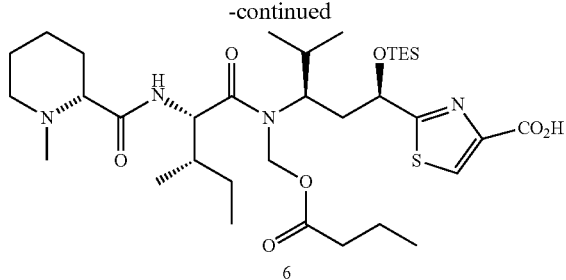

Large Scale Synthesis of Tripeptide Acid 6.

To 2 L of 0.05 M phosphate (pH=7.4) at 30° C. was added 3.6 g of porcine liver esterase (17 units/mg). 3.0 g of methyl ester 4 was dissolved in 100 mL of DMSO. The first 50 mL of this solution was added at a rate of 1.1 mL/h, and the second half was added at a rate of 1.2 mL/h via syringe pump. After the addition was complete, the reaction mixture was allowed to stir at 30° C. for several hours. HPLC of an EtOAc extract of the reaction mixture showed the reaction was complete. The reaction mixture was drained from the reactor in 1 L portions and extracted with 94% EtOAc-6% MeOH (vol./vol.) solution (3×1 L). The combined extracts were washed with brine, dried over $Na_2SO_4$ and concentrated under reduced pressure. 2.8 g of product 6 was recovered (95%). The product appeared to be clean by UPLC analysis, except for pentafluorophenol carried over from the previous reaction, Large Scale Synthesis of Tubulysin B.

3.0 g (4.30 mmol) of tripeptide 6 was dissolved in 18 mL THF and 0.70 mL (4.30 mmol) of $3HF.NEt_3$ was added and the reaction mixture stirred for 30 minutes. LC-MS analysis (10% to 100% acetonitrile, pH 7 buffer) confirmed complete deprotection of the TES group. THF was removed under reduced pressure. The residue was dried under high vacuum for 5 minutes. The crude product was dissolved in 18 mL dry pyridine. 6.11 mL (64.50 mmol, 15 equiv) of $Ac_2O$ was added at 0° C. The resulting clear solution was stirred at room temperature for 5 hours. LC-MS analysis (10% to 100% acetonitrile, pH 7.0) indicated >98% conversion. 117 mL of dioxane/$H_2O$ was added and the resulting mixture stirred at room temperature for 1 hour. The mixture was concentrated under reduced pressure. The residue was co-evaporated with toluene (3×) and dried under high vacuum overnight. Crude product 7 was used directly for the next reaction. LCMS (ESI) $[M+H]^+$ 625.2; the NMR spectral data was consistent with structure 7.

Method B. The crude tripeptide acid 7 (2.67 g, 4.30 mmol) was dissolved in 43 mL of DCM (anhydrous), 1.59 g (8.6 mmol, 2.0 equiv) of pentafluorophenol was added, followed by 9.33 g (21.5 mmol, 5.0 equiv) of DCC on the resin. The resulting reaction mixture was stirred at room temperature for 16 hours. LC-MS analysis indicated >96% conversion. The reaction mixture was filtered and concentrated to dryness, dried under high vacuum for 5 minutes. The residue was dissolved in 16.5 mL DMF, Tut-HCl (1.45 g, 5.59 mmol, 1.3 equiv) was added, followed by DIPEA (4.88 mL, 27.95 mmol, 6.5 equiv). The resulting clear solution was stirred at room temperature for 10 minutes. The reaction mixture was purified on prep-HPLC (X-bridge column, 50 mM $NH_4HCO_3$, 25% to 100%, six runs). The pure fractions were combined, the acetonitrile was removed under reduced pressure, the residue was extracted with EtOAc (2×) and the combined EtOAc extracts dried over $Na_2SO_4$. The EtOAc was removed under reduced pressure. The residue was dried under high vacuum for 1 hour to yield 1.35 g of desired product (38% combined yield from 4). NMR spectral data was consistent with the tubulysin B.

What is claimed is:

1. A process for preparing a compound of the formula

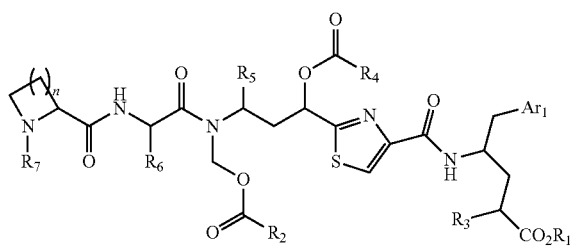

or a pharmaceutically acceptable salt thereof;
wherein
$Ar_1$ is 4-hydroxyphenyl;
$R_1$ is hydrogen, benzyl, or C1-C4 alkyl;
$R_2$ is C1-C8 alkyl or C3-C8 cycloalkyl;
$R_3$ is C1-C4 alkyl;
$R_4$ is C1-C8 alkyl or C3-C8 cycloalkyl;
$R_5$ and $R_6$ are each independently branched C3-C6 alkyl;
$R_7$ is C1-C6 alkyl; and
n is 1, 2, 3, or 4;
wherein the process comprises
the step of treating a compound of formula A with triethylsilyl chloride and imidazole in a solvent selected from the group consisting of tetrahydrofuran (THF), 2,5-dimethyl-tetrahydrofuran, 2-methyl-tetrahydrofuran, tetrahydropyran, diethyl ether, t-butyl methyl ether, dimethyl formamide, N-methylpyrrolidinone (NMP), and dichloromethane, where $R_8$ is C1-C6 unbranched alkyl

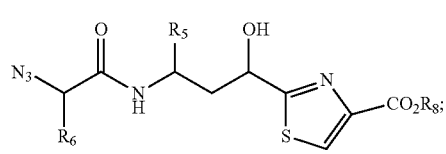

or
the step of treating a compound of formula B with a base and a compound of the formula $ClCH_2OC(O)R_2$ in a solvent selected from the group consisting of tetrahydrofuran, 2,5-dimethyl-tetrahydrofuran, 2-methyl-tetrahydrofuran, tetrahydropyran, diethyl ether, t-butyl methyl ether, dimethyl formamide, N-methylpyrrolidinone, and dichloromethane at a temperature from about −78° C. to about 0° C.; wherein the molar ratio of the compound of the formula $ClCH_2OC(O)R_2$ to the compound of formula B from about 1 to about 1.5, where $R_8$ is C1-C6 unbranched alkyl

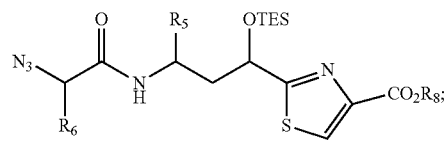

or
the steps of
a) preparing a compound of formula (E1), where $X_1$ is selected from the group consisting of N-hydroxysuccinimide, N-hydroxyphthalimide, 4-nitrophenol, pentafluorophenol, 2-pyridinol, 1-hydroxybenzotriazole, 1-hydroxy-7-aza-benzotriazole, and cyanomethanol, from a compound of formula E

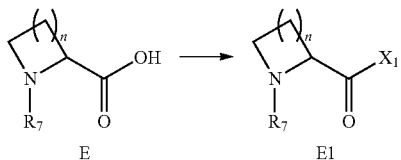

and
b) treating a compound of formula C under-reducing hydrogenation conditions in the presence of the compound of formula E1, where $R_8$ is C1-C6 unbranched alkyl

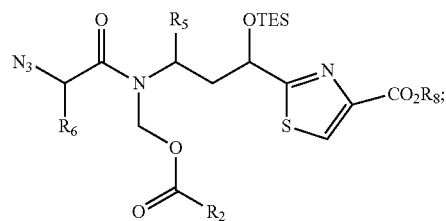

or
the step of treating compound D with an esterase, where $R_8$ is C1-C6 unbranched alkyl

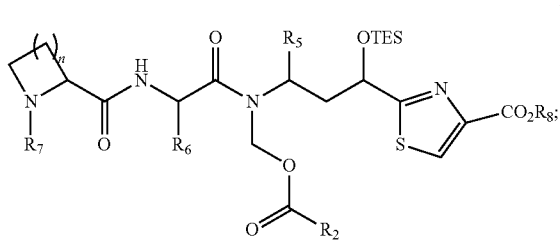

or
the step of treating the silyl ether of compound F with a non-basic fluoride reagent selected from the group consisting of Et₃N.3HF and HF-pyridine

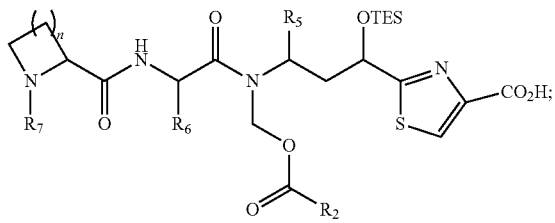

F or
the step of treating a compound of formula G with an acylating agent of formula R₄C(O)X₂, where X₂ is —OC(O)R₄

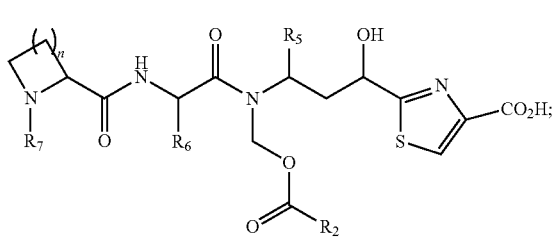

G or
the steps of
c) forming an active ester intermediate from a compound of formula H

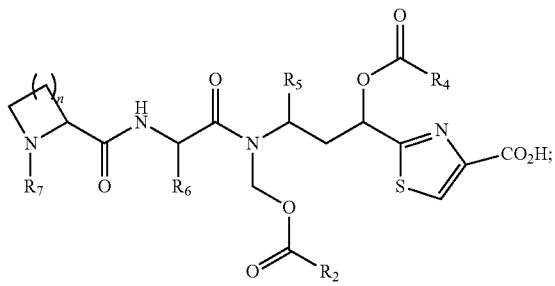

H and
d) reacting the active ester intermediate with a compound of the formula I

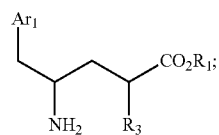

or combinations thereof.

2. The process of claim 1 comprising the step of treating a compound of formula A with triethylsilyl chloride and imidazole in a solvent selected from the group consisting of tetrahydrofuran, 2,5-dimethyl-tetrahydrofuran, 2-methyl-tetrahydrofuran, tetrahydropyran, diethyl ether, t-butyl methyl ether, dimethyl formamide, N-methylpyrrolidinone, and dichloromethane, where R₈ is C1-C6 unbranched alkyl

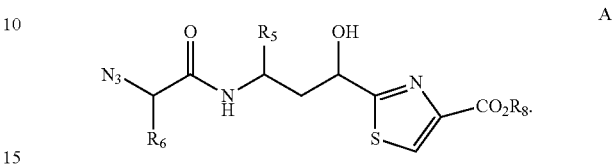

A

3. The process of claim 1 comprising the step of treating a compound of formula B with a base and a compound of the formula ClCH₂OC(O)R₂ in a solvent selected from the group consisting of tetrahydrofuran, 2,5-dimethyl-tetrahydrofuran, 2-methyl-tetrahydrofuran, tetrahydropyran, diethyl ether, t-butyl methyl ether, dimethyl formamide, N-methylpyrrolidinone, and dichloromethane at a temperature from about −78° C. to about 0° C.; wherein the molar ratio of the compound of the formula ClCH₂OC(O)R₂ to the compound of formula B from about 1 to about 1.5, where R₈ is C1-C6 unbranched alkyl

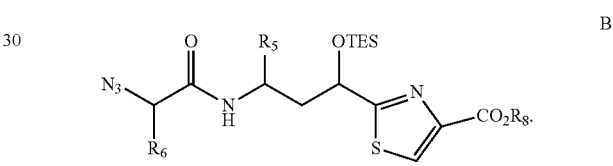

B

4. The process of claim 1 comprising the steps of
a) preparing a compound of formula (E1), where X₁ is selected from the group consisting of N-hydroxysuccinimide, N-hydroxyphthalimide, 4-nitrophenol, pentafluorophenol, 2-pyridinol, 1-hydroxybenzotriazole, 1-hydroxy-7-aza-benzotriazole, and cyanomethanol, from a compound of formula E

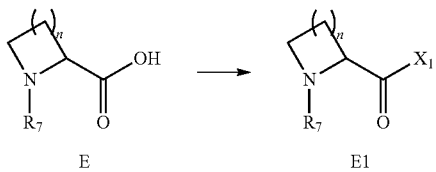

E          E1 and
b) treating a compound of formula C under hydrogenation conditions in the presence of the compound of formula E1, where R₈ is C1-C6 unbranched alkyl

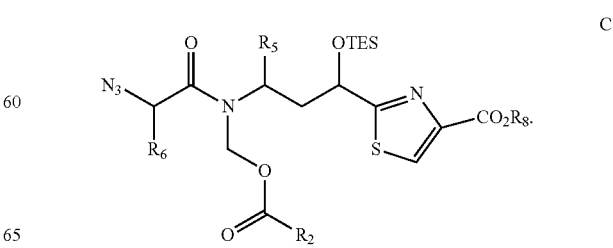

C

5. The process of claim 1 comprising the step of treating compound D with an esterase, where $R_8$ is C1-C6 unbranched alkyl

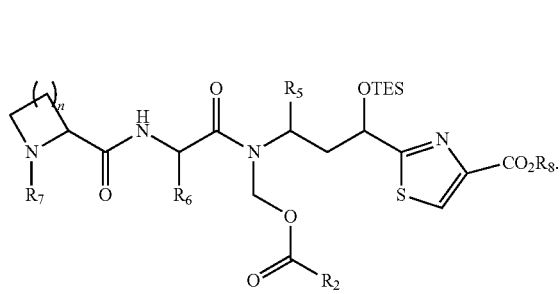

6. The process of claim 1 comprising the step of treating the silyl ether of compound F with a non-basic fluoride reagent selected the group consisting of $Et_3N \cdot 3HF$ and HF-pyridine

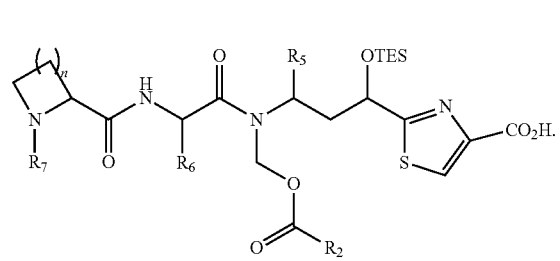

7. The process of claim 1 comprising the step of treating a compound of formula G with an acylating agent of formula $R_4C(O)X_2$, where $X_2$ is $-OC(O)R_4$

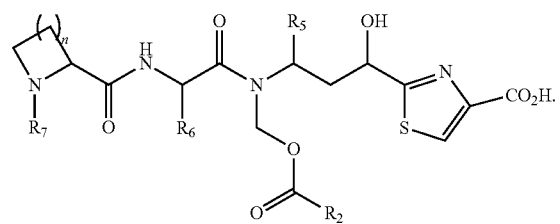

8. The process of claim 1 comprising the steps of
c) forming an active ester intermediate from a compound of formula H

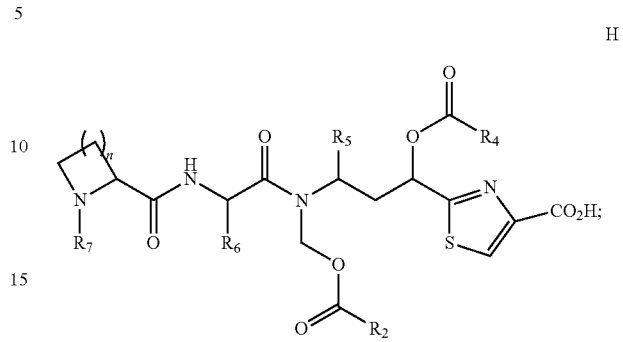

and
d) reacting the active ester intermediate with a compound of the formula I

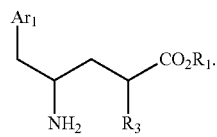

9. The process of claim 1, wherein $R_1$ is hydrogen.
10. The process of claim 1, wherein $R_2$ is n-butyl.
11. The process of claim 1, wherein $R_3$ is methyl.
12. The process of claim 1, wherein $R_4$ is methyl.
13. The process of claim 1, wherein $R_5$ is iso-propyl.
14. The process of claim 1, wherein $R_6$ is sec-butyl.
15. The process of claim 1, wherein $R_7$ is methyl.
16. The process of claim 1, wherein $R_1$ is hydrogen, $R_2$ is n-butyl, $R_3$ is methyl, $R_4$ is methyl, $R_5$ is iso-propyl, $R_6$ is sec-butyl and $R_7$ is methyl.
17. The process of claim 1, wherein $R_2$ is $CH_2CH(CH_3)_2$, $CH_2CH_2CH_3$, $CH_2CH_3$, $CH=C(CH_3)_2$ or $CH_3$.
18. The process of claim 17, wherein $R_2$ is $CH_2CH_2CH_3$.
19. The process of claim 1, wherein $R_1$ is hydrogen, $R_2$ is $CH_2CH(CH_3)_2$, $CH_2CH_2CH_3$, $CH_2CH_3$, $CH=C(CH_3)_2$, or $CH_3$, $R_3$ is methyl, $R_4$ is methyl, $R_5$ is iso-propyl, $R_6$ is sec-butyl and $R_7$ is methyl.
20. The process of claim 1, wherein $R_1$ is hydrogen, $R_2$ is n-propyl, $R_3$ is methyl, $R_4$ is methyl, $R_5$ is iso-propyl, $R_6$ is sec-butyl and $R_7$ is methyl.

* * * * *